(12) United States Patent
Lieberman et al.

(10) Patent No.: US 7,696,179 B2
(45) Date of Patent: Apr. 13, 2010

(54) INHIBITION OF GENE EXPRESSION USING RNA INTERFERING AGENTS

(75) Inventors: Judy Lieberman, Brookline, MA (US); Manjunath Narasimhaswamy, Roslindale, MA (US); Erwei Song, Guangzhou (CN); Sang-Kyung Lee, Seoul (KR); Premlata Shankar, Roslindale, MA (US)

(73) Assignee: Immune Disease Institute, Inc., Boston, MA (US)

( * ) Notice: Subject to any disclaimer, the term of this patent is extended or adjusted under 35 U.S.C. 154(b) by 646 days.

(21) Appl. No.: 10/533,621

(22) PCT Filed: Oct. 29, 2003

(86) PCT No.: PCT/US03/34424

§ 371 (c)(1),
(2), (4) Date: Feb. 15, 2006

(87) PCT Pub. No.: WO2004/039957

PCT Pub. Date: May 13, 2004

(65) Prior Publication Data

US 2006/0293262 A1    Dec. 28, 2006

Related U.S. Application Data

(60) Provisional application No. 60/422,419, filed on Oct. 29, 2002.

(51) Int. Cl.
*A01N 63/00* (2006.01)
*A61K 48/00* (2006.01)

(52) U.S. Cl. .................... 514/44; 424/93.2; 435/455; 514/55

(58) Field of Classification Search ................ None
See application file for complete search history.

(56) References Cited

U.S. PATENT DOCUMENTS

| 2002/0061585 | A1 | 5/2002 | Eagles et al. | |
| 2003/0125241 | A1* | 7/2003 | Wissenbach et al. | 514/8 |
| 2004/0248296 | A1* | 12/2004 | Beresford et al. | 435/375 |

FOREIGN PATENT DOCUMENTS

| JP | 11-292795 | * | 10/1999 |
| WO | WO 03/099298 A1 | | 4/2003 |

OTHER PUBLICATIONS

Kitabwalla, M. and R.M. Ruprecht. (Oct. 24, 2002) RNA Interference—A New Weapon Against HIV and Beyond. New England Journal of Medicine, v. 347(17):1364-1367.*
Deeks, S.G., and Walker, B.D. (2007) Human Immunodeficiency Virus Controllers: Mechanisms of Durable Virus Control in the Absence of Antiretroviral Therapy. Immunity, v.27:406-416.*
Novina, et al. (2002) siRNA-Directed Inhibition of HIV-1 Infection. Nature Medicine, v.8(7):681-686.*
Bass, B. (2001) The Short Answer. Nature, v.411:428-9.*
Elbashir, et al. (2001) Functional Anatomy of siRNAs for Mediating Efficient RNAi in *Drosophila melanogaster* Embryo Lysate. The EMBO Journal, v.20(23):6877-88.*
Elbashir, et al. (2001) Duplexes of 21-Nucleotide RNAs Mediate RNA Interference in Cultured Mammalian Cells. Nature, v.411:494-8.*
Martinez, et al. Supression of Chemokine Receptor Expression by RNA Interference Allows for Inhibition of HIV-1 Replication. AIDS, 2002, vol. 16, pp. 2385-2390.
Deng et al. Identification of a major co-receptor for primary isolates of HIV-1 (1996) *Nature* 381:661-666.
Nansen et al. The role of CC chemokine receptor 5 in antiviral immunity (2002) *Blood* 99:1237-1245.
Samson, et al. Resistance to HIV-1 infection in caucasian individuals bearing mutant alleles of the CCR-5 chemokine receptor gene (1996) *Nature* 382:722-725.
Steinberger et al. Functional deletion of the CCR5 receptor by intracellular immunization produces cells that are refractory to CCR5-dependent HIV-1 infection and cell fusion (2000) *Proc. Natl. Acad. Sci.* USA. 97:805-10.
Lieberman, Judy et al., "Interfering with disease: opportunities and roadblocks to harnessing RNA interference" Trends in Molecular Magazine 9(9):397-403, 2003.

(Continued)

*Primary Examiner*—Richard Schnizer
*Assistant Examiner*—Jennifer Pitrak
(74) *Attorney, Agent, or Firm*—Nixon Peabody LLP

(57) ABSTRACT

The present invention is based, at least in part, on the discovery of compositions and methods for the treatment and prevention of infectious diseases or disorders, e.g., HIV infection, AIDS, and AIDS-related diseases. In particular, the present invention pertains to methods of modulating cellular gene expression or protein activity, e.g., CCR5, gene expression or protein activity and/or gene expression or protein activity of a gene or sequence of an infectious agent, in order to treat or prevent infectious diseases or disorders, HIV infection, AIDS, or an AIDS-related disease or disorder. In one embodiment the combination of an RNA interfering agent targeting a cellular gene in combination with an RNA interfering agent targeting a gene or sequence of an infectious agent results in prolonged prevention of infection by an infectious agent. The present invention is based on the identification of novel RNA interference agents, e.g., siRNA molecules, which target cellular genes, e.g., chemokine receptors, e.g., the CCR5 gene, and result in inhibition of target gene expression on target gene expressing cells, thereby inhibiting entry of infectious agents, e.g., HIV infection into target cells, prevention infection, and/or suppressing replication in established infection.

2 Claims, 10 Drawing Sheets

OTHER PUBLICATIONS

Zhang, D. et al., "Physical and Functional Interaction between Myeloid Cell Leukemia 1 Protein (MCL1) and Fortilin" J Bio Chem 277(40):37430-37438, 2002.

Novina, C. D. et al., "siRNA-directed inhibition of HIV-1 infection" Nature Medicine 8(7):681-686, 2002 and "Corigendum" Errata and Corrigenda Nature Medicine 9(11):1433, 2003.

Lee, N. S. et al., "Expression of small interfering RNAs targeted against HIV-1 rev transcripts in human cells" Nature Biotechnology 19:500-505, 2002.

Kitabwalla, M. and Ruprecht, R. M., "RNA Interference—A New Weapon Against HIV and Beyond" N Engl J Med 347(17):1364-1367, 2002.

Song, E. et al., "Sustained Small Interfering RNA-Mediated Human Immunodeficiency Virus Type 1 Inhibition in Primary Macrophages" J Virol 77(13):7174-7181, 2003.

\* cited by examiner

```
                              SEQUENCE LISTING

<160> NUMBER OF SEQ ID NOS: 31

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 1
cucugcuucg gugucgaaat ttttt                                               25

<210> SEQ ID NO 2
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 2
uuucgacacc gaagcagagt ttttt                                               25

<210> SEQ ID NO 3
<211> LENGTH: 21
<212> TYPE: DNA
<213> ORGANISM: Artificial Sequence
<220> FEATURE:
<223> OTHER INFORMATION: synthetic oligonucleotides

<400> SEQUENCE: 3
gauuguacug agagacaggc u                                                   21

<210> SEQ ID NO 4
<211> LENGTH: 23
<212> TYPE: DNA
<213> ORGANISM: Artificial Sequence
<220> FEATURE:
<223> OTHER INFORMATION: synthetic oligonucleotides

<400> SEQUENCE: 4
ccugucucuc ucaguacaau cuu                                                 23

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotides

<400> SEQUENCE: 5
ggcuacgucc aggagcgcac c                                                   21

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotides

<400> SEQUENCE: 6
```
ugcgcuccug gacguagccu u                                             21

<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotides

<400> SEQUENCE: 7
atggattatc aagtgtcaag tcc                                           23

<210> SEQ ID NO 8
<211> LENGTH: 24
<212> TYPE: DNA
<213> ORGANISM: Artificial Sequence
<220> FEATURE:
<223> OTHER INFORMATION: synthetic oligonucleotides

<400> SEQUENCE: 8
ccagaattga tactgactgt atgg                                          24

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotides

<400> SEQUENCE: 9
tctgtcaggg ttggaaagtc                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotides

<400> SEQUENCE: 10
aaatgcaaac cgcttccaac                                               20

<210> SEQ ID NO 11
<211> LENGTH: 2888
<212> TYPE: DNA
<213> ORGANISM: Mus musculus

<400> SEQUENCE: 11
agatttgtac agctctccta gccagaggag gtgagacatc cgttcccct  acaagagact    60
ctggctcttg caggatggat tttcaagggt cagttccgac ctatagctat gacatcgatt   120
atggtatgtc agcaccctgc caaaaaatca atgtgaaaca aattgcggct cagctcctgc   180
ccccactcta ctccctggta ttcatctttg gttttgtggg taacatgatg gtcttcctca   240
tcttgataag ctgcaaaaag ctgaagagcg tgactgatat ctacctgctc aacctggcca   300
tctctgacct gctcttcctg ctcacactac cattctgggc tcactatgct gcaaatgagt   360
gggtctttgg gaacataatg tgtaaagtat tcacagggct ctatcacatt ggttattttg   420
gtggaatctt cttcattatc ctcctgacaa ttgataggta cttggctatt gtccatgctg   480
tgtttgcttt aaaagtcaga acggtcaact ttgggggtgat aacaagtgta gtcacttggg   540
cggtggctgt gtttgcctct ctcccagaaa taatctttac cagatctcag aaagaaggtt   600
tcattatac atgcagtcct catttccac acactcagta tcatttctgg aagagtttcc   660

```
aaacattaaa gatggtcatc ttgagcctga tcctgcctct acttgtcatg gtcatctgct    720
actcaggaat tctccacacc ctgtttcgct gtaggaatga aagaagagg cacagggctg     780 tgaggctcat ctttgccatc atgattgtct actttctctt ctggactccc tacaacattg    840
tcctcctcct gaccaccttc caggaattct ttggactgaa taactgcagt agttctaata    900
gactagacca ggccatgcag gcaacagaga ctcttggaat gacacactgc tgcctaaacc    960
ctgtcatcta tgcctttgtt ggagagaagt tccggagtta tctctcagtg ttcttccgaa   1020
aacacatggt caaacgcttt tgcaaacggt gttcaatttt ccagcaagac aatcctgatc   1080
gtgcaagctc agtctatacc cgatccacag gagaacatga agtttctact ggtttatgac   1140
ctggttgact tttgtgtatc acgtattttt ctatgcagct tgggagtagg aatggttctt   1200
ttaaaaaaag aaattagtat catagagggc ccaagataca tgcatctttt tgatatttat   1260
ttttagatag attgggtctc ttaaaactga atggggaggt tggggtggag gagcagggag   1320
aacgagtctt ttatcagggc cggaaatat gcacaaagag acttgaggca ggtgccatga    1380
cccatatgca aagggacgga cacagggccg atgctgtggc ctagagatga cgtgtctcac   1440
cgctgggttc ctgaaagcgg ctgtaaatat gcctgattgc cataaagtcg cttcttgctg   1500
tctatggatg tgcctgactg ccaacaggga agaaccactt ctgcctataa aacgtaagtc   1560
agcagaactt ggggtaaatc ggagttagag gtgcataaga accctaggc ttagttaggt    1620 tgaaataccc attgaggaaa cagcaaatac aaaggaagaa taagagtt agccgggaag     1680 gtagtctcat tttacagccg gaatataatg ttatctcagg ctagcatttt gttcctgcct   1740
tcagacctaa atcctaccac accgggactg tgaacacctg gattatgaat catgagcctg   1800
aggtctagga ataataataa cgtttgtgat tttagatgag ggctgtttcc atagtttgaa   1860
gccagaactt tatcatcttg agcagaagct ccaagagatg aggaaagagc accaattttt   1920 ctctaatta cttagcagtc atcatctctg gaagattcat tttagaaaca agttgttgtg    1980
cccctcagaa gccatgagag tataacgact gctctctgtg ttccaggctg agtatgagga   2040
cttcagtcac actttccaga tggcttctcc acacaaacaa tgctaagttt ggccatttca   2100
gaggtttagg attttttgtt gtttttgcag ttgatatttt gaattttaga gcagttgaga   2160
tcttcctagt gaaggctaga ggaggaaaga aaggggttag aatctctcag gagattaaag   2220
tttctgccta acaagaggtg ttactggttt ttctcaagct ccgattgtga aaccagaggc   2280
ctgggactgt cagcaggaag tgagcatttg cttttcttc cttgtgatcc acattcctcc    2340
ccactctgtt gctcagctgg cgtcaagctc acgatcctcc tgcttacatc tcaagttctg   2400
agattacaag tatatgtgaa catatccagc ggttatttta ttcattagca tatagaaagt   2460
tatacgttct ttgaagataa tgagtcttat aaaaagtgct ttgtaaaaaa aattgcattt   2520
tatactttca atcaagtgta catttagtga gtagtacgta aaattatgag agtattttgt   2580
aagtagttgt tttggagaac gcccccaata atacttgttt aaatatagcg ttcttggatt   2640
aagtgggtgg tggtgatgat aatatttcct tgaaagtatt tttagccgtt aactttcttc   2700
cttaaacaat ttttcataat aatttgttct taaagatgtt atgtccaagc atgcagtttc   2760
ggagcagtgt tgcttgaaa gagtgtaaat tttaaattgt gcttactctc aatcaaaaga    2820
gttttaacat atttacgaat ttatttcaga agtcaagaat ctggttgaaa ataaagatat   2880
gcaactta                                                           2888
```

<210> SEQ ID NO 12

```
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 12
guguagucac uuggguggut ttttt                                          25

<210> SEQ ID NO 13
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 13
accacccaag ugacuacact ttttt                                          25

<210> SEQ ID NO 14
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 14
uagacuagac caggccaugt ttttt                                          25

<210> SEQ ID NO 15
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 15
cauggccugg ucuagucuat ttttt                                          25

<210> SEQ ID NO 16
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 16
acgcuuuugc aaacggugut ttttt                                          25

<210> SEQ ID NO 17
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 17
acaccguuug caaaagcgut ttttt                                          25

<210> SEQ ID NO 18
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 18
```

```
gacaauccug aucguguaat ttttt                                          25
```

<210> SEQ ID NO 19
<211> LENGTH: 25
<212> TYPE: DNA
<213> ORGANISM: Artificial Sequence
<220> FEATURE:
<223> OTHER INFORMATION: synthetic oligonucleotides

<400> SEQUENCE: 19

```
uuacacgauc aggauuguct ttttt                                          25
```

<210> SEQ ID NO 20
<211> LENGTH: 9
<212> TYPE: PRT
<213> ORGANISM: HIV-1

<400> SEQUENCE: 20

Arg Lys Lys Arg Arg Gln Arg Arg Arg
 1               5

<210> SEQ ID NO 21
<211> LENGTH: 13
<212> TYPE: PRT
<213> ORGANISM: HIV-1

<400> SEQUENCE: 21

Gly Arg Lys Lys Arg Arg Gln Arg Arg Arg Thr Pro Gln
 1               5                  10

<210> SEQ ID NO 22
<211> LENGTH: 11
<212> TYPE: PRT
<213> ORGANISM: HIV-1

<400> SEQUENCE: 22

Tyr Gly Arg Lys Lys Arg Arg Gln Arg Arg Arg
 1               5                  10

<210> SEQ ID NO 23
<211> LENGTH: 26
<212> TYPE: PRT
<213> ORGANISM: Homo sapiens

<400> SEQUENCE: 23

Ala Ala Val Ala Leu Leu Pro Ala Val Leu Leu Ala Leu Leu Ala Pro
 1               5                  10                  15

Val Gln Arg Lys Arg Gln Lys Leu Met Pro
            20                  25

<210> SEQ ID NO 24
<211> LENGTH: 17
<212> TYPE: PRT
<213> ORGANISM: Caiman crocodylus

<400> SEQUENCE: 24

Met Gly Leu Gly Leu His Leu Leu Val Leu Ala Ala Ala Leu Gln Gly
 1               5                  10                  15

Ala

<210> SEQ ID NO 25
<211> LENGTH: 23
<212> TYPE: PRT

```
<213> ORGANISM: HIV-1

<400> SEQUENCE: 25

Gly Ala Leu Phe Leu Gly Phe Leu Gly Ala Ala Gly Ser Thr Met Gly
1               5                   10                  15

Ala Pro Lys Ser Lys Arg Lys
            20

<210> SEQ ID NO 26
<211> LENGTH: 16
<212> TYPE: PRT
<213> ORGANISM: Drosophila

<400> SEQUENCE: 26

Arg Gln Ile Lys Ile Trp Phe Gln Asn Arg Arg Met Lys Trp Lys Lys
1               5                   10                  15

<210> SEQ ID NO 27
<211> LENGTH: 5
<212> TYPE: PRT
<213> ORGANISM: HIV-1
<220> FEATURE:
<221> NAME/KEY: VARIANT
<222> LOCATION: 1,5
<223> OTHER INFORMATION: Xaa may be any amino acid

<400> SEQUENCE: 27

Xaa Arg Gly Asp Xaa
1               5

<210> SEQ ID NO 28
<211> LENGTH: 24
<212> TYPE: PRT
<213> ORGANISM: Influenza

<400> SEQUENCE: 28

Gly Leu Phe Glu Ala Ile Ala Gly Phe Ile Glu Asn Gly Trp Glu Gly
1               5                   10                  15

Met Ile Asp Gly Gly Gly Tyr Cys
            20

<210> SEQ ID NO 29
<211> LENGTH: 27
<212> TYPE: PRT
<213> ORGANISM: Artificial Sequence
<220> FEATURE:
<223> OTHER INFORMATION: synthetic oligonucleotides

<400> SEQUENCE: 29

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 30
<211> LENGTH: 8
<212> TYPE: PRT
<213> ORGANISM: Artificial Sequence
<220> FEATURE:
<223> OTHER INFORMATION: synthetic oligonucleotides

<400> SEQUENCE: 30

Asp His Gln Leu Asn Pro Ala Phe
1               5
```

```
<210> SEQ ID NO 31
<211> LENGTH: 8
<212> TYPE: PRT
<213> ORGANISM: Homo sapiens

<400> SEQUENCE: 31

Phe Cys Tyr Trp Lys Thr Cys Thr
1               5
```

INHIBITION OF GENE EXPRESSION USING RNA INTERFERING AGENTS

CROSS-REFERENCE TO RELATED APPLICATIONS

This application is a U.S. National Phase Entry Under 35 U.S.C. §371 of International Application No. PCT/US2003/034424, filed Oct. 29, 2003, which designated the U.S., and which claimed benefit under 35 U.S.C. §119 of U.S. Provisional Patent Application No. 60/422,419, filed Oct. 29, 2002.

GOVERNMENT RIGHTS

This invention was made at least in part with government support under grant nos. AI49792, AI145306, AI46566, and AI42519 awarded by the National Institutes of Health (NIH). The government has certain rights in this invention.

BACKGROUND OF THE INVENTION

The human retrovirus, human immunodeficiency virus (HIV), causes Acquired Immunodeficiency Syndrome (AIDS), an incurable disease in which the body's immune system breaks down leaving the victim vulnerable to opportunistic infections, e.g., pneumonia, and certain cancers, e.g., Kaposi's Sarcoma. AIDS is a major global health problem. The Joint United Nations Programme on HIV/AIDS (UN-AIDS) estimates that there are now over 34 million people living with HIV or AIDS worldwide, some 28.1 million of those infected individuals reside in impoverished sub-Saharan Africa. In the United States, approximately one out of every 500 people are infected with HIV or have AIDS. Since the beginning of the epidemic, AIDS has killed nearly 19 million people worldwide, including some 425,000 Americans. AIDS has replaced malaria and tuberculosis as the world's deadliest infectious disease among adults and is the fourth leading cause of death worldwide.

The molecular mechanism of HIV entry into cells involves specific interactions between the viral envelope glycoproteins (env) and two target cell proteins, CD4 and the chemokine receptors. HIV cell tropism is determined by the specificity of the env for a particular chemokine receptor, a 7 transmembrane-spanning, G protein-coupled receptor (Steinberger et al., (2000) *Proc. Natl. Acad. Sci. USA*. 97: 805-10). The two major families of chemokine receptors are the CXC chemokine receptors and the CC chemokine receptors (CCR) so named for their binding of CXC and CC chemokines, respectively. While CXC chemokine receptors traditionally have been associated with acute inflammatory responses, the CCRs are mostly expressed on cell types found in connection with chronic inflammation and T-cell-mediated inflammatory reactions: eosinophils, basophils, monocytes, macrophages, dendritic cells, and T cells (Nansen, et al. 2002, *Blood* 99:4). It has been shown that CC chemokine receptor 5 (CCR5) represents the major co-receptor for primary Macrophage-cell-line-tropic (M-tropic) HIV strains (Deng et al. (1996) *Nature* 381:661). M-tropic strains predominate during the asymptotic phase of the disease in infected individuals (Samson, et al. (1996) *Nature* 382:722). Eventually, however, HIV can become dual-tropic. Such strains are capable of recognizing the CXCR4 protein on CD4-bearing T-cells. During this phase HIV-1 may infect both macrophages and T-cells. Still later, the bulk of the viral population may switch it's preference to the CXCR4 receptor and become T-cell-line-tropic (T-tropic). T-tropic viruses readily destroy infected T-cells, contributing to the collapse of the immune system and the onset of AIDS which leads to opportunistic infections, neurological disease, neoplastic growth and eventual death.

SUMMARY OF THE INVENTION

The present invention is based, at least in part, on the discovery of compositions and methods for the prevention and treatment of an infectious disease or disorder, e.g., a viral infection, e.g., HIV infection, by, e.g., modulating gene expression or protein activity, e.g., cellular gene expression or protein activity and/or expression or protein activity of a gene or sequence of an infectious agent, in order to treat or prevent infection. In one embodiment, the cellular gene is a chemokine receptor.

In one aspect of the invention, it has been shown that of one or more cellular RNA interfering agents, e.g., siRNAs, in combination with one or more RNA interfering agents, e.g., siRNAs, targeting a gene or sequence of an infectious agent such as a gag siRNA, have a synergistic effect and completely suppress infection and/or replication, e.g., HIV infection and/or replication, for a prolonged period of time, e.g., for two or more weeks.

Accordingly, the present invention provides novel RNA interfering agents, e.g., siRNA molecules, which result in inhibition of target gene or sequence, e.g., CCR5 expression on, e.g., cells expressing the target gene or sequence, e.g., macrophages. In one embodiment, the RNA interfering agents of the invention inhibit entry of infection, e.g., HIV infection, into target cells, preventing infection. In another embodiment, the RNA interfering agents of the invention suppresses viral replication in established infection, e.g., HIV infection.

Accordingly, in one aspect, the invention provides a composition comprising an RNA interfering agent which inhibits expression of a target gene or sequence, e.g., CCR5, through RNA interference (RNAi) or post-transcriptional gene silencing (PTGS). In one embodiment, the agent is an RNA which is homologous to the target gene, e.g., the CCR5 gene, or a fragment thereof. In another embodiment, the agent is a double-stranded, short interfering RNA (siRNA) which is homologous to the target gene. In still another embodiment, the siRNA is about 19 nucleotides to about 28 nucleotides in length, preferably about 19 nucleotide to about 25 nucleotides in length, and more preferably about 21 nucleotides in length. In a further embodiment, the siRNA is double stranded and contains a 3' overhang on each strand. In one embodiment, the overhang comprises about 1 to about 6 nucleotides on each strand, preferably about 2 nucleotides on each strand.

In a preferred embodiment, the agent is a synthetic siRNA. In one embodiment, the siRNA is a double stranded siRNA, wherein the first strand comprises the sequence of SEQ ID NO:1 and the second strand comprises the sequence of SEQ ID NO:2. In another embodiment, the siRNA is capable of inducing or regulating degradation of mRNA, e.g., CCR5 mRNA. In still another embodiment, the siRNA inactivates the target gene or sequence, e.g., CCR5, by post-transcriptional silencing. In yet another embodiment, the siRNA further comprises a poly-G tail.

In another aspect, the invention provides a vector comprising a short interfering RNA (siRNA) which is homologous to the target gene or sequence and is capable of promoting RNA interference of the target gene or sequence. In still another aspect, the invention provides a vector comprising a DNA template which encodes an RNA which is homologous to the target gene or sequence and is capable of promoting RNA interference, e.g., CCR5 RNA interference. In yet another aspect, the invention provides a cell transfected with a vector comprising the RNA interfering agent, e.g., siRNA of the invention or a DNA template which encodes an RNA of the invention.

In another aspect, the invention provides methods of inhibiting gene expression in a subject or modulating an immune response, e.g., an immune response modulated by, for example, a chemokine receptor, e.g., a CCR5-modulated immune response, in a subject comprising administering to the subject an RNA interfering agent, e.g., an siRNA, which modulates target gene expression. The invention also provides methods of preventing or treating an infectious disease or disorder in a subject comprising administering to the subject an RNA interfering agent, e.g., an siRNA which modulates CCR5 gene expression.

In a further aspect, the invention also provides methods of inhibiting entry of a virus into a cell, e.g., a cell expressing a target gene, e.g., a chemokine receptor, e.g., CCR5, comprising administering to the cell an RNA interfering agent, e.g., siRNA, which modulates target gene expression. In one embodiment, the RNA interfering agent, e.g., siRNA, is administered intravenously. In another embodiment, the RNA interfering agent, e.g., siRNA is topically administered to a mucosal membrane of the subject, e.g., as a microbicide. In one embodiment, the siNRAs are mixed with a basic peptide prior to administration. In another embodiment, the siRNAs are encapsulated in liposomes prior to administration.

In still a further aspect, the invention provides methods of inhibiting entry of an infectious agent into a cell, e.g., a macrophage, expressing a target gene or inhibiting infection, e.g., viral infection, comprising administering to the cell one or more RNA interfering agents, e.g., siRNAs, which modulate cellular gene expression or activity and one or more RNA interfering agents, e.g., siRNAs, which modulate expression or activity of a gene or sequence of an infectious agent, e.g., HIV gene expression. In another aspect, the invention provides methods of treating or preventing infection in a subject comprising administering to the subject one or more RNA interfering agents, e.g., siRNAs, which modulate, e.g., inhibit, cellular gene expression, e.g., CCR5 gene expression or activity and one or more RNA interfering agents, e.g. siRNAs, which modulate, e.g., inhibit, gene expression or activity of a gene or sequence of an infectious agent. In one embodiment, the RNA interfering agents, e.g., siRNAs which modulate gene expression, modulate, e.g., gag gene expression, vif gene expression, or nef gene expression. In another embodiment, the RNA interfering agents, e.g., siRNAs, are administered intravenously. The RNA interfering agents, e.g., siRNAs may be administered simultaneously or serially. In a further embodiment, the RNA interfering agents, e.g., siRNAs are topically administered to a mucosal membrane of the subject, e.g., as a microbicide. The RNA interfering agents may be administered prior to, during, or after infection by an infectious agent.

Other features and advantages of the invention will be apparent from the following detailed description and claims.

DETAILED DESCRIPTION OF THE INVENTION

Figure 1A:
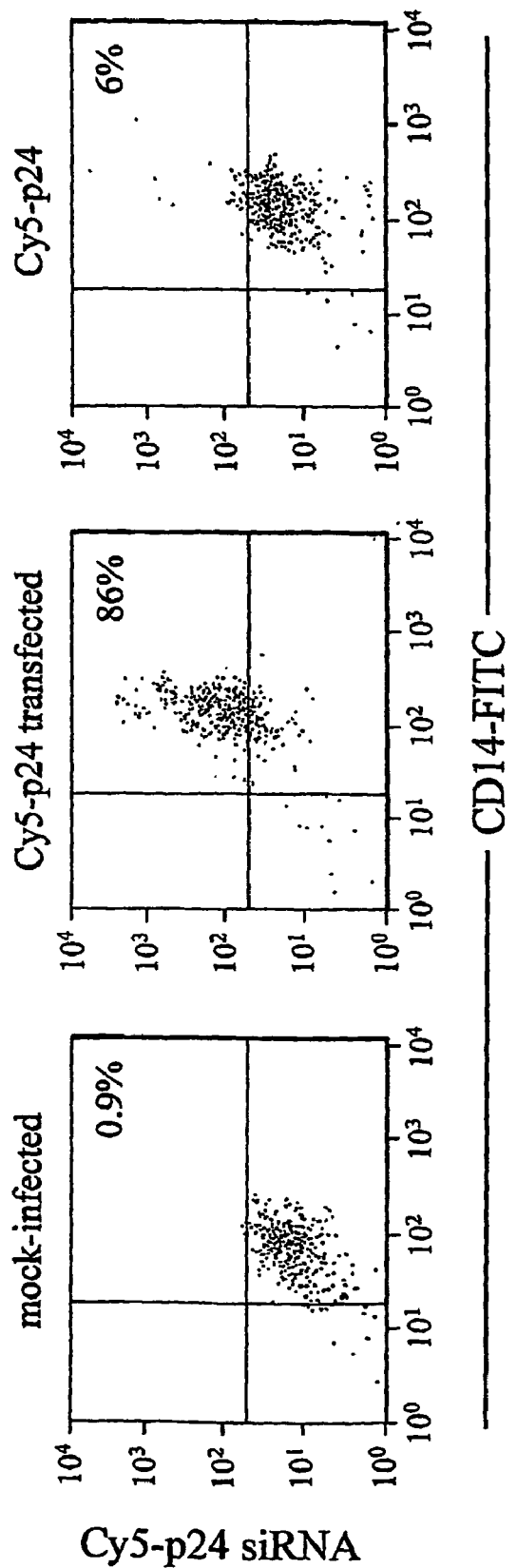
FIG. 1. CCR5- and p24 siRNAs prevent $HIV_{BaL}$ infection in MDMs a. MDMs were either left unexposed or incubated or transfected with Cy5-labeled p24 siRNA for 24 hours, stained with CD14-FITC and analyzed by flow cytometry. The percentage of Cy5+ cells is indicated in each panel. b. MDMs were either mock-transfected (filled-in diamond) or transfected with GFP-(■), p24–(▲), CCR5-(x) or p24+ CCR5 (*) siRNAs and infected after 2 days with $HIV_{BaL}$ for indicated number of days. Cell free virus production was measured by p24 ELISA. c. Fluorescent microscopy (×200) of MDMs in-situ hybridized for HIV-1 RNA with a fluorescin-labeled probe (lower panel) and counterstained with Texas Red-X Phalloidin (upper panel) 7 days after infection. d. Cells were stained with p24-FITC 15 days after infection and examined by flow cytometry. Percentage of p24+ cells is shown in each panel.

The present invention is based, at least in part, on the discovery of compositions and methods for the prevention and/or treatment of an infectious disease or disorder, e.g., a viral infection, e.g., HIV infection, by, e.g., modulating gene expression or protein activity, e.g., cellular gene expression or protein activity and/or gene expression or protein activity of a gene or sequence expressed by an infectious agent, in order to treat or prevent infection, e.g., HIV infection, AIDS, or an AIDS-related disease or disorder, in a subject. In particular, the present invention pertains to compositions and methods of modulating the gene expression or protein activity of one or more cellular target molecules, e.g., CCR5 gene expression or protein activity, and/or modulating the gene expression or protein activity of one or more target molecules of an infectious agent, e.g., viral target molecules, e.g., gag gene, in order to treat or prevent an infectious disease or disorder, e.g., a viral or bacterial infection, e.g., HIV infection, AIDS, or an AIDS-related disease or disorder.

In one aspect of the invention, it has been shown that of one or more cellular RNA interfering agents, e.g., siRNAs, in combination with one or more RNA interfering agents targeting a gene or sequence of an infectious agent, e.g., siRNAs, such as a p24 siRNA, have a synergistic effect and efficiently suppress infection and/or replication, e.g., HIV infection and/ or replication, for a prolonged period of time, e.g. two or more weeks. Therefore, the present invention is based on the discovery that administration of one or more RNA interfering agents, e.g., siRNA molecules, which target a cellular gene, including, for example, a chemokine receptor, e.g., CCR5, in combination with one or more RNA interfering agents, e.g., siRNA molecules, which target a viral gene, e.g., an HIV gene, including, for example, p24, inhibits infection and/or replication, e.g., HIV infection and/or replication. In one embodiment, inhibition of infection and/or replication may be for a prolonged period of time, e.g., about two or more weeks. Accordingly, in one embodiment of the invention, the combination of one or more RNA interfering agents, e.g., siRNAs, targeted to a cellular gene or sequence, with one or more RNA interfering agents, e.g., siRNAs, targeted to a gene or sequence of an infectious agent, e.g., an HIV viral gene or sequence is used to treat and/or prevent infection and/or replication by, e.g., a virus, e.g., HIV. The methods and compositions of the invention are not limited to treatment and prevention of HIV, but encompass treatment and prevention of any infectious disease or disorder as described herein.

In one aspect, the invention provides a method for preventing in a subject, an infectious disease or disorder, by administering to the subject one or more therapeutic agents, e.g., the RNA interfering agents as described herein. For example, the RNA interfering agents described herein may be used as microbicides to substantially reduce transmission of diseases transmitted by microbes, such as, for example, sexually transmitted infections (STIs), e.g., hepatitis, e.g., HBV, HCV, HGV, human papilloma virus (HPV), herpes (HSV-2), other viral infections, and/or bacterial infections. For example, the RNA interfering agent(s) may be administered to the mucosal membrane of the subject. Subjects at risk for an infectious disease or disorder, can be identified by, for example, any known risk factors for an infectious disease or disorder.

The present invention is also based, at least in part, on the identification of novel RNA interfering agents, e.g., siRNA molecules, which target a cellular gene or sequence, e.g., a chemokine receptor gene, and result in inhibition of cellular gene expression on the cellular gene expressing cells, e.g., macrophages, thereby inhibiting entry of an infectious agent, e.g., a virus, e.g., HIV, into target cells, preventing infection, and suppressing viral replication in established infection, e.g., HIV infection.

In one aspect of the invention, it has been found that an RNA interfering agent, e.g., an siRNA targeted to a cellular gene which is expressed by a macrophage, e.g., a chemokine receptor, e.g., CCR5, remains within macrophages, which are terminally differentiated, non-dividing cells, for a longer period of time than siRNAs directed to target molecules of an infectious agent, e.g., viral genes, e.g., HIV viral genes. Therefore, siRNAs targeted to genes expressed by macrophages, e.g. CCR5, provide prolonged protection from infection, e.g., viral infection such as HIV infection, e.g., through sustained knockdown of the cellular gene, e.g., CCR5. While not intending to be bound by theory, it is proposed that the continued presence of the substrate RNA, e.g., CCR5, may be necessary for intracellular persistence of siRNA, and thus may be needed to prolong RNA interference of the target gene, e.g., CCR5, and inhibition of the virus, e.g., HIV, entry into the cell. It has also been shown that the siRNA effect rapidly fades in dividing cell lines even in the presence of target mRNAs. Furthermore, CCR5 may represent a desirable target because homozygous expression of a nonfunctional allele of CCR5 has no deleterious immunological consequences, but provides protection against HIV infection. Therefore, genes expressed by non-dividing macrophages, e.g., CCR5, represent preferred targets for RNA interfering agents, e.g., siRNAs which inhibit gene expression by RNA interference. Accordingly, RNA interfering agents, e.g., siRNAs, directed to genes expressed by macrophages, e.g., CCR5, represents a preferred therapeutic and prophylactic agent against viral infection, including HIV infection, AIDS, and AIDS-related diseases or disorders. It is to be understood that the RNA interfering agents of the invention are not limited to those which target molecules expressed by macrophages. Cellular targets include molecules expressed by any cell type, including, but not limited to, T-cells, eosinophils, basophils, monocytes, macrophages, and dendritic cells.

An "RNA interfering agent" as used herein, is defined as any agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA Apr; 9(4):493-501 incorporated be reference herein).

In one embodiment, the siRNA may target a specific genetic mutation in a target gene.

The target gene may be a gene or sequence of an infectious agent, e.g., a viral gene, or cellular gene, or a fragment thereof. An siRNA may be substantially homologous to the target gene or genomic sequence, or a fragment thereof. As used herein, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues may be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives.

The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated.

Any cellular molecule (also referred to herein as "host cell molecule") involved in or related to the initiation or progression of infectious disease or disorder, or a symptom thereof, may be modulated by the compositions and methods of the invention. For example, cellular targets of the RNA interfering agents of the invention, (also referred to herein as "host cell targets"), include, but are not limited to, any cellular molecule involved in the entry or transport of any infectious agent or portion thereof, e.g., any viral or bacterial infectious agent, or other infectious agent, e.g., HV, into any cell, or any cellular molecule which is involved in the life cycle, replication, or pathogenicity of any infectious agent. Cellular targets include cellular receptors and co-receptors, e.g., chemokine receptors. Chemokine receptors include, for example, CXC chemokine receptors and the CC chemokine receptors (CCRs), e.g., CXCR2, CXCR4, CCR8, CCR9, CCR5, CCR4, CCR3, CCR2, and CCR1. Other receptors include STRL33, US28, V28, gpr1, gpr15, Apj, ChemR23, etc. Any other cell surface molecule, e.g., CD26, VPAC1, etc., or any molecules which produce these molecules, e.g., enzymes that synthesize heparin sulfate proteoglycans, galactoceramides, etc., are also included as cellular targets Also included as cellular targets are cellular enzymes that are involved in the viral life cycle, e.g., the HIV life cycle, including, but not limited to, RNA polymerase II, N-myristoyltransferase, glycosylation enzymes, gp160-processing enzymes, ribonucleotide reductase, enzymes involved in polyamine biosynthesis, proteins involved in viral budding, etc. Other cellular targets include cellular transcription factors, cytokines and second messengers, e.g., TNFα, IL-1α, phospholipase C, protein kinase C, proteins involved in regulating intracellular calcium, and cellular accessory molecules.

As used herein the phrase "target molecule of an infectious agent" or "gene or sequence of an infectious agent" includes any gene or sequence contained within the genome of an infectious agent or any other transcript produced during the life cycle of the agent which is, for example, involved in the replication, pathogenicity, or infection by the agent. The target molecule of the infectious agent should be specific to the infectious agent, i.e., it should have a sequence which differs from a gene or sequence normally present in the host cell.

The term "infectious agent" includes any virus (DNA or RNA virus), bacteria, fungus, or protozoa which is capable of infection. For example, infectious agents include HIV, CMV, RSV, HSV, yellow fever virus, dengue fever virus, Japanese encephalitis virus, Murray Valley encephalitis, polioviruis, SARS, influenza, rhinovirus, west nile virus, Ebola virus, foot and mouth virus, papilloma virus infection, other sexually transmitted diseases such as, but not limited to hepatitis, e.g., HBV, HCV, HGV, human papilloma virus (HPV), herpes (HSV-2), Epstein-Barr virus (EBV), and/or bacteria, fungus, or protozoa Accordingly, a target molecule of an infectious agent includes any gene or sequences contained within any virus (DNA or RNA virus), bacteria, fungus, or protozoa which is capable of infection, e.g., HIV, CMV, RSV, HSV, yellow fever virus, dengue fever virus, Japanese encephalitis virus, Murray Valley encephalitis, polioviruis, influenza, rhinovirus, west nile virus, Ebola virus, foot and mouth virus, papilloma virus infection, other sexually transmitted diseases such as, but not limited to hepatitis, e.g., HBV, HCV, HGV, human papilloma virus (HPV), herpes (HSV-2), Epstein-Barr virus (EBV), and/or bacteria, fungus, or protozoa. In one embodiment, a target molecule of an infectious agent includes, for example, any gene or sequence contained within the HIV genome, e.g., transcripts encoding any viral proteins including p24, other gag proteins p6, p2, and p1, polymerase (p61, p55), reverse transcriptase, RNase H, protease, integrase, envelope, tat, rev, nef, vif, vpu, vpx, and/or tev.

As used herein, a bacterial infectious agent includes a variety of bacterial organisms, including gram-positive and gram-negative bacteria. Examples include, but are not limited to, *Neisseria* spp, including *N. gonorrhea* and *N. meningitidis*, *Streptococcus* spp, including *S. pneumoniae*, *S. pyogenes*, *S. agalactiae*, *S. mutans*; *Haemophilus* spp, including *H. influenzae* type B, non typeable *H. influenzae*, *H. ducreyi*; *Moraxella* spp, including *M catarrhalis*, also known as *Branhamella catarrhalis*; *Bordetella* spp, including *B. pertussis*, *B. parapertussis* and *B. bronchiseptica*; *Mycobacterium* spp., including *M. tuberculosis, M. bovis, M. leprae, M. avium, M. paratuberculosis, M. smegmatis; Legionella* spp, including *L. pneumophila*; *Escherichia* spp, including enterotoxic *E. coli*, enterohemorragic *E. coli*, enteropathogenic *E. coli*; *Vibrio* spp, including *V. cholera*, *Shigella* spp, including *S. sonnei, S. dysenteriae, S. flexnerii*; *Yersinia* spp, including *Y. enterocolitica, Y. pestis, Y. pseudotuberculosis*, *Campylobacter* spp, including *C. jejuni* and *C. coli*; *Salmonella* spp, including *S. typhi, S. paratyphi, S. choleraesuis, S. enteritidis*; *Listeria* spp., including *L. monocytogenes*; *Helicobacter* spp, including *H. pylori*; *Pseudomonas* spp, including *P. aeruginosa*, Staphylococcus spp., including *S. aureus*, *S. epidermidis*; Enterococcus spp., including *E. faecalis*, *E. faecium*; Clostridium spp., including *C. tetani*, *C. botulinum*, *C. difficile*; Bacillus spp., including *B. anthracis*; Corynebacterium spp., including *C. diphtheriae*; Borrelia spp., including *B. burgdorferi*, *B. garinii*, *B. afzelii*, *B. andersonii*, *B. hermsii*; Ehrlichia spp., including *E. equi* and the agent of the Human Granulocytic Ehrlichiosis; Rickettsia spp, including *R. rickettsii*; Chlamydia spp., including *C. trachomatis*, *C. neumoniae*, *C. psittaci*; Leptsira spp., including *L. interrogans*; Treponema spp., including *T. pallidum*, *T. denticola*, *T. hyodysenteriae*. Preferred bacteria include, but are not limited to, Listeria, mycobacteria, mycobacteria (e.g., *tuberculosis*), Anthrax, Salmonella and *Listeria monocytogenes*.

As used herein, the term "infectious disease or disorder" is defined as any disease, disorder, or infection which is caused by or related to infection by any infectious agent. For example, infectious diseases or disorders include diseases or disorders caused by or related to infection by a viral infectious agent, bacterial infectious agent, fungal infectious agent, or protozoal infectious agent. Examples of infectious diseases or disorders include, but are not limited to diseases or disorders caused by or related to a viral infectious agent, e.g., HIV, AIDS-related dementia, AIDS-related cancers such as Kaposi's sarcoma, non-Hodgkin's lymphoma, primary central nervous system lymphoma, and invasive squamous cell cancer, AIDS-related diseases or disorders, viral infections including, but not limited to CMV, RSV, HSV, yellow fever virus, dengue fever virus, Japanese encephalitis virus, Murray Valley encephalitis, polioviruis, influenza, rhinovirus, west nile virus, Ebola virus, foot and mouth virus, cytomegalovirus (esp. Human), Rotavirus, Epstein-Barr virus, Varicella Zoster Virus, paramyxoviruses: Respiratory Syncytial virus, parainfluenza virus, measles virus, mumps virus, or influenza virus, human papilloma viruses (for example HPV6, 11, 16, 18 and the like), other sexually transmitted diseases such as, but not limited to hepatitis, e.g., HBV, HCV, HGV, and herpes (HSV-2).

An "AIDS-related disease or disorder" is defined as any disease, disorder, or infection caused by or related to infection of a cell or an organism, e.g. a human, with the HIV virus, e.g., HIV-1 or HIV-2. Examples of AIDS-related diseases or disorders include, but are not limited to, AIDS-related dementia, AIDS-related cancers such as Kaposi's sarcoma, non-Hodgkin's lymphoma, primary central nervous system lymphoma, and invasive squamous cell cancer, AIDS-related infections including, but not limited to *Mycobacterium avium* complex (MAC), wasting syndrome, fungal infections, gastrointesinal manifestations, pneumonia, fatigue, fever, nausea, kidney disorders, musculoskeletal disorders, or any other disease or disorder associated with HIV infection or diminished immune system function caused by HIV infection.

As used herein, the term "subject" includes an individual susceptible to infection with an infectious agent.

Various aspects of the invention are described in further detail in the following subsections:

I. Short Interfering RNAs (siRNAs) of the Invention

In particular, the present invention relates to siRNA or shRNA molecules of about 15 to about 40 or about 15 to about 28 nucleotides in length, which are homologous to a target gene or sequence and mediate RNAi of the target gene or sequence. Preferably, the siRNA molecules have a length of about 19 to about 25 nucleotides. More preferably, the siRNA molecules have a length of about 19, 20, 21, or 22 nucleotides. The siRNA molecules of the present invention can also comprise a 3' hydroxyl group. The siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the RNA molecule is double stranded, one strand has a 3' overhang and the other strand can be blunt-ended or have an overhang. In the embodiment in which the RNA molecule is double stranded and both strands comprise an overhang, the length of the overhangs may be the same or different for each strand. In a particular embodiment, the RNA of the present invention comprises about 19, 20, 21, or 22 nucleotide strands which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

A. Design and Preparation of siRNA Molecules

Synthetic siRNA molecules of the present invention can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) *Nature* 411:494-498; Elbashir, S. M., W. Lendeckel and T. Tuschl (2001) *Genes & Development* 15:188-200; Harborth, J. et al. (2001) *J. Cell Science* 114:4557-4565; Masters, J. R. et al. (2001) *Proc. Natl. Acad. Sci. USA* 98:8012-8017; and Tuschl, T. et al. (1999) *Genes & Development* 13:3191-3197). Alternatively, several commercial RNA synthesis suppliers are available including, but not limited to, Proligo (Hamburg, Germany), Dharmacon Research (Lafayette, Co., USA), Pierce Chemical (part of *Perbio Science*, Rockford, Ill., USA), Glen Research (Sterling, Va., USA), ChemGenes (Ashland, Mass., USA), and Cruachem (Glasgow, UK). As such, siRNA molecules are not difficult to synthesize and are readily provided in a quality suitable for RNAi.

The targeted region of the siRNA molecule of the present invention can be selected from a given target gene sequence, e.g., a cellular or viral target sequence, e.g., a chemokine receptor, e.g., CCR5, a gag gene, e.g., p24 antigen, and the like, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (where N can be any nucleotide) and selecting sequences with at least 25%, 30%, 35%, 40%, 45%, 50%, 55%, 60%, 65%, 70% or 75% G/C content. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but not limited to the NCBI, BLAST, Derwent and GenSeq as well as commercially available oligosynthesis companies such as Oligoengine®, may also be used to select siRNA sequences against EST libraries to ensure that only one gene is targeted.

II. Delivery of RNA Interfering Agents

Methods of delivering RNA interfering agents, e.g., siRNAs of the present invention or vectors containing the siRNAs of the present invention, to the target cells, e.g., macrophages or CD4+ T cells or other hematopoietic cells, for uptake include injection of a composition containing the agent, e.g., the siRNA, or directly contacting the cell, e.g., the macrophage or CD4+ T cell, or an organism, with a composition comprising the agent, e.g., the siRNA. A viral-mediated delivery mechanism may also be employed to deliver agents, e.g., siRNAs, to cells in vitro and in vivo as described in Xia, H. et al. (2002) *Nat Biotechnol* 20(10):1006). Other methods of introducing siRNA molecules of the present invention to target cells, e.g., macrophages or CD4+ T cells, include a variety of art-recognized techniques including, but not limited to, calcium phosphate or calcium chloride co-precipitation, DEAE-dextran-mediated transfection, lipofection, or electroporation as well as a number of commercially available transfection kits (e.g., OLIGOFECTAMINE® Reagent from Invitrogen) (see, e.g. Sui, G. et al. (2002) *Proc. Natl. Acad. Sci., USA* 99:5515-5520; Calegari, F. et al. (2002) *Proc. Natl. Acad. Sci., USA Oct.* 21, 2002 [electronic publication ahead of print]; J-M Jacque, K. Triques and M. Stevenson (2002) *Nature* 418:435-437; and Elbashir, S. M et al. (2001) supra). Suitable methods for transfecting a target cell, e.g., a macrophage or CD4+ T cell, can also be found in Sambrook, et al. (*Molecular Cloning: A Laboratory Manual.* 2nd, ed., *Cold Spring Harbor Laboratory*, Cold Spring Harbor Laboratory Press, Cold Spring Harbor, N.Y., 1989), and other laboratory manuals. The efficiency of transfection may depend on a number of factors, including the cell type, the passage number, the confluency of the cells as well as the time and the manner of formation of siRNA-liposome complexes (e.g., inversion versus vortexing). These factors can be assessed and adjusted without undue experimentation by one with ordinary skill in the art.

An siRNA may be introduced along with components that perform one or more of the following activities: enhance siRNA uptake by the cell, e.g., macrophages or CD4+ T cells, inhibit annealing of single strands, stabilize single strands, or otherwise facilitate delivery to the target cell and increase inhibition of the target gene, e.g., CCR5. For example, a poly-G tail may be added to one or more ends of the siRNA for uptake into target cells, e.g., macrophages or CD4+ T cells. Moreover, the siRNA may be fluoro-derivatized and delivered to the target cell as described by Capodici, et al. ((2002) *J. Immuno.* 169(9):5196).

An RNA interfering agent, e.g., an siRNA, may be directly introduced into the cell, e.g., macrophage or CD4+ T cell, or introduced extracellularly into a cavity, interstitial space, into the circulation of an organism, introduced orally, or may be introduced by bathing a cell or organism in a solution containing the agent, e.g., siRNA. An RNA interfering agent, e.g., an siRNA, may also be introduced into cells via topical application to a mucosal membrane. Vascular or extravascular circulation, the blood or lymph system, and the cerebrospinal fluid are also sites where the RNA interfering agent, e.g., siRNA, may be introduced.

A further method of treating cells with siRNA is an ex vivo method wherein cells to be treated with siRNA, e.g., macrophages or CD4+ T cells, are obtained from the individual using known methods (e.g., phlebotomy or collection of bone marrow) and one or more siRNAs that mediate target gene inhibition are introduced into the cells, which are then re-introduced into the individual. If necessary, biochemical components needed for RNAi to occur can also be introduced into the cells.

In another embodiment, RNA may also be engineered for expression in bone marrow derived stem cells to generate HIV resistant immune cells, e.g., macrophages.

Another aspect of the invention pertains to vectors, for example, recombinant expression vectors, containing a nucleic acid encoding an RNA of the present invention, e.g., one or more siRNA targeting a cellular gene and/or one or more siRNAs targeting a gene or sequence of an infectious agent, e.g., a viral gene, e.g., a CCR5 siRNA, a p24 siRNA, or both. As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retrovises, lentiviruses, adenoviruses and adeno-associated viruses), which serve equivalent functions. In a preferred embodiment, lentiviruses are be used to deliver one or more siRNA molecules of the present invention to a cell, e.g., a macrophage, T cell, dendritic cell, or hematopoietic stem cell.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the target cell, the level of expression of siRNA desired, and the like.

The expression vectors of the invention can be introduced into target cells to thereby produce siRNA molecules of the present invention. In one embodiment, a DNA template, e.g., a DNA template encoding a target gene, may be ligated into an expression vector under the control of RNA polymerase III (Pol III), and delivered to a target cell. Pol III directs the synthesis of small, noncoding transcripts which 3' ends are defined by termination within a stretch of 4-5 thymidines. The expression vector may either express sense and antisense strands separately or as a hairpin structure. The hairpin RNA (also referred to as a stem-loop; antisense strand followed by a short (~5 basepair) loop followed by a sense strand) is believed to be processed endogenously by Dicer to an effective siRNA. Hairpin sequences may be introduced into retroviral and lentiviral vectors. Accordingly, DNA templates may be used to synthesize, in vivo, siRNAs which effect RNAi (Sui, et al. (2002) PNAS 99(8):5515).

In another embodiment, the compositions of the invention are provided as a surface component of a lipid aggregate, such as a liposome, or are encapsulated by a liposome. Liposomes, which can be unilamellar or multilamellar, can introduce encapsulated material into a cell by different mechanisms. For example, the liposome can directly introduce its encapsulated material into the cell cytoplasm by fusing with the cell membrane. Alternatively, the liposome can be compartmentalized into an acidic vacuole (i.e., an endosome) and its contents released from the liposome and out of the acidic vacuole into the cellular cytoplasm. In one embodiment the invention features a lipid aggregate formulation of the compounds described herein, including phosphatidylcholine (of varying chain length; e.g., egg yolk phosphatidylcholine), cholesterol, a cationic lipid, and 1,2-distearoyl-sn-glycero3-phosphoethanolamine-polythyleneglycol-2000 (DSPE-PEG2000). The cationic lipid component of this lipid aggregate can be any cationic lipid known in the art such as dioleoyl 1,2,-diacyl trimethylammonium-propane (DOTAP). In another embodiment, polyethylene glycol (PEG) is covalently attached to the compositions of the present invention. The attached PEG can be any molecular weight but is preferably between 2000-50,000 daltons.

As used herein, the term "target cell" is intended to refer to a cell into which an RNA interfering agent, e.g., an siRNA molecule of the invention, including a recombinant expression vector encoding an RNA interfering agent, e.g., an siRNAs of the invention, has been introduced. The terms "target cell" and "host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. Preferably, a target cell is a mammalian cell, e.g., a human cell. In particularly preferred embodiments, it is a macrophage or $CD4^+$ T cell.

Dentritic cells (DCs) and macrophages may be specifically targeted, taking advantage of the unique properties of these cells, which are constantly sampling the environment and have special receptors for uptake of anionic polymers and phosphatidyl serine (PS) on apoptotic cells. siRNA packaged into liposomes may be used as a delivery method specifically targeting DCs and macrophages. In one embodiment, various ratios of lipid to siRNA may be utilized. Liposome composition may also be modified to incorporate varying concentrations of PS to enhance uptake via the PS receptor used for the recognition and phagocytosis of apoptotic cells (Fadok, Va., et al. (2000). *Nature,* 405, 85-90; Fadok, Va., and Chimini, G. (2001). *Semin Immunol,* 13, 365-372; Hoffmann, P R, et al. (2001). *J Cell Biol,* 155, 649-659; Huynh, M L, et al. (2002). *J Clin Invest,* 109, 41-50).

To produce liposomes, phospholipids in chloroform/methanol (90:10) are dried under nitrogen, resuspended in PBS containing various concentrations of duplex Cy5-labeled siRNA and sonicated for 3 hours at 4° C. The liposomes are added to MDMs (Huynh, M L, et al. (2002). *J Clin Invest,* 109, 41-50). The transfection efficiency is determined after overnight culture and washing by epifluorescence microscopy and quantitated by flow cytometry. In another embodiment, a polyG tail of about 5-10 nucleotides in length may be added to the 5' end of the sense strand of the siRNA to enhance uptake via the macrophage scavenger receptor (Srividya, S, et al (2000). *Biochem Biophys Res Commun,* 268, 772-777).

In another embodiment of the invention, the RNA interfering agents of the invention may be transported or conducted across biological membranes using carrier polymers which comprise, for example, contiguous, basic subunits, at a rate higher than the rate of transport of RNA interfering agents, e.g., siRNA molecules, which are not associated with carrier polymers. Combining a carrier polymer with an RNA interfering agents, e.g., an siRNA, with or without a cationic transfection agent, results in the association of the carrier polymer and the RNA interfering agent, e.g., siRNA. The carrier polymer may efficiently deliver the RNA interfering agent, e.g., siRNA, across biological membranes both in vitro and in vivo. Accordingly, the invention provides methods for delivery of an RNA interfering agent, e.g., an siRNA, across a biological membrane, e.g., a cellular membrane including, for example, a nuclear membrane, using a carrier polymer. The invention also provides compositions comprising an RNA interfering agent, e.g., an siRNA, in association with a carrier polymer. The term "associated" as used herein in reference to the association of an RNA interfering agent and a carrier polymer, refers to an association by a direct linkage or an indirect linkage, by covalent or chemical linkage or by an electrostatic bond.

The term "polymer" as used herein, refers to a linear chain of two or more identical or non-identical subunits joined by covalent bonds. A peptide is an example of a polymer that can be composed of identical or non-identical amino acid subunits that are joined by peptide linkages.

The term "peptide" as used herein, refers to a compound made up of a single chain of D- or L-amino acids or a mixture of D- and L-amino acids joined by peptide bonds. Generally, peptides contain at least two amino acid residues and are less than about 50 amino acids in length.

The term "protein" as used herein, refers to a compound that is composed of linearly arranged amino acids linked by peptide bonds, but in contrast to peptides, has a well-defined conformation. Proteins, as opposed to peptides, generally consist of chains of 50 or more amino acids.

"Polypeptide" as used herein, refers to a polymer of at least two amino acid residues and which contains one or more peptide bonds. "Polypeptide" encompasses peptides and proteins, regardless of whether the polypeptide has a well-defined conformation.

In one embodiment, carrier polymers in accordance with the present invention contain short-length polymers of from about 6 to up to about 25 subunits. The carrier is effective to enhance the transport rate of the RNA interfering agent across the biological membrane relative to the transport rate of the biological agent alone. Although exemplified polymer compositions are peptides, the polymers may contain non-peptide backbones and/or subunits as discussed further below.

In an important aspect of the invention, the carrier polymers of the invention are particularly useful for transporting biologically active agents across cell or organelle membranes, when the RNA interfering agents are of the type that require transmembrane transport to exhibit their biological effects. As a general matter, the carrier polymer used in the methods of the invention preferably includes a linear backbone of subunits. The backbone will usually comprise heteroatoms selected from carbon, nitrogen, oxygen, sulfur, and phosphorus, with the majority of backbone chain atoms usually consisting of carbon. Each subunit may contain a sidechain moiety that includes a terminal guanidino or amidino group.

Although the spacing between adjacent sidechain moieties will usually be consistent from subunit to subunit, the polymers used in the invention can also include variable spacing between sidechain moieties along the backbone.

The sidechain moieties extend away from the backbone such that the central guanidino or amidino carbon atom (to which the $NH_2$ groups are attached) is linked to the backbone by a sidechain linker that preferably contains at least 2 linker chain atoms, more preferably from 2 to 5 chain atoms, such that the central carbon atom is the third to sixth chain atom away from the backbone. The chain atoms are preferably provided as methylene carbon atoms, although one or more other atoms such as oxygen, sulfur, or nitrogen can also be present. Preferably, the sidechain linker between the backbone and the central carbon atom of the guanidino or amidino group is 4 chain atoms long, as exemplified by an arginine side chain.

The carrier polymer sequence of the invention can be flanked by one or more non-guanidino/non-amidino subunits, or a linker such as an aminocaproic acid group, which do not significantly affect the rate of membrane transport of the corresponding polymer-containing conjugate, such as glycine, alanine, and cysteine, for example. Also, any free amino terminal group can be capped with a blocking group, such as an acetyl or benzyl group, to prevent ubiquitination in vivo.

The carrier polymer of the invention can be prepared by straightforward synthetic schemes. Furthermore, the carrier polymers are usually substantially homogeneous in length and composition, so that they provide greater consistency and reproducibility in their effects than heterogenous mixtures.

According to an important aspect of the present invention, association of a single carrier polymer to an RNA interfering agent, e.g., an siRNA, is sufficient to substantially enhance the rate of uptake of an agent across biological membranes, even without requiring the presence of a large hydrophobic moiety in the conjugate. In fact, attaching a large hydrophobic moiety may significantly impede or prevent cross-membrane transport due to adhesion of the hydrophobic moiety to the lipid bilayer. Accordingly, the present invention includes carrier polymers that do not contain large hydrophobic moieties, such as lipid and fatty acid molecules.

In one embodiment, the transport polymer is composed of D or L amino acid residues. Use of naturally occurring L-amino acid residues in the transport polymers has the advantage that break-down products should be relatively non-toxic to the cell or organism. Preferred amino acid subunits are arginine (α-amino-delta.-guanidi-novaleric acid) and α-amino-ε-amidinohexanoic acid (isosteric amidino analog). The guanidinium group in arginine has a pKa of about 12.5.

More generally, it is preferred that each polymer subunit contains a highly basic sidechain moiety which (i) has a pKa of greater than 11, more preferably 12.5 or greater, and (ii) contains, in its protonated state, at least two geminal amino groups (NH2) which share a resonance-stabilized positive charge, which gives the moiety a bidentate character.

Other amino acids, such as α-amino-β-guanidinopropionic acid, α-amino-.gamma.-guanidinobutyric acid, or α-amino-ε-guanidinocaproic acid can also be used (containing 2, 3 or 5 linker atoms, respectively, between the backbone chain and the central guanidinium carbon).

D-amino acids may also be used in the transport polymers. Compositions containing exclusively D-amino acids have the advantage of decreased enzymatic degradation. However, they may also remain largely intact within the target cell. Such stability is generally not problematic if the agent is biologically active when the polymer is still attached. For agents that are inactive in conjugate form, a linker that is cleavable at the site of action (e.g., by enzyme- or solvent-mediated cleavage within a cell) should be included to promote release of the agent in cells or organelles.

Any peptide, e.g., basic peptide, or fragment thereof, which is capable of crossing a biological membrane, either in vivo or in vitro, is included in the invention. These peptides can be synthesized by methods known to one of skill in the art. For example, several peptides have been identified which may be used as carrier peptides in the methods of the invention for transporting RNA interfering agents across biological membranes. These peptides include, for example, the homeodomain of antennapedia, a *Drosophila* transcription factor (Wang et al., (1995) *PNAS USA.*, 92, 3318-3322); a fragment representing the hydrophobic region of the signal sequence of Kaposi fibroblast growth factor with or without NLS domain (Antopolsky et al. (1999) *Bioconj. Chem.*, 10, 598-606); a signal peptide sequence of caiman crocodylus Ig(5) light chain (Chaloin et al. (1997) *Biochem. Biophys. Res. Comm.*, 243, 601-608); a fusion sequence of HIV envelope glycoprotein gp4114, (Morris et al. (1997) *Nucleic Acids Res.*, 25, 2730-2736); a transportan A-achimeric 27-mer consisting of N-terminal fragment of neuropeptide galanine and membrane interacting wasp venom peptide mastoporan (Lindgren et al., (2000), *Bioconjugate Chem.*, 11, 619-626); a peptide derived from influenza virus hemagglutinin envelop glycoprotein (Bongartz et al., 1994, *Nucleic Acids Res.*, 22, 468 1 4688); RGD peptide; and a peptide derived from the human immunodeficiency virus type-1 ("HIV-1"). Purified HIV-1 TAT protein is taken up from the surrounding medium by human cells growing in culture (A. D. Frankel and C. O. Pabo, (1988) *Cell*, 55, pp. 1189-93). TAT protein trans-activates certain HIV genes and is essential for viral replication. The full-length HIV-1 TAT protein has 86 amino acid residues. The HIV tat gene has two exons. TAT amino acids 1-72 are encoded by exon 1, and amino acids 73-86 are encoded by exon 2. The full-length TAT protein is characterized by a basic region which contains two lysines and six arginines (amino acids 47-57) and a cysteine-rich region which contains seven cysteine residues (amino acids 22-37). The basic region (i.e., amino acids 47-57) is thought to be important for nuclear localization. Ruben, S. et al., *J. Virol.* 63: 1-8 (1989); Hauber, J. et al., *J. Virol.* 63 1181-1187 (1989); Rudolph et al. (2003) 278(13):11411. The cysteine-rich region mediates the formation of metal-linked dimers in vitro (Frankel, A. D. et al., *Science* 240: 70-73 (1988); Frankel, A. D. et al., *Proc. Natl. Acad. Sci USA* 85: 6297-6300 (1988)) and is essential for its activity as a transactivator (Garcia, J. A. et al., *EMBO J.* 7:3143 (1988); Sadaie, M. R. et al., *J. Virol.* 63: 1 (1989)). As in other regulatory proteins, the N-terminal region may be involved in protection against intracellular proteases (Bachmair, A. et al., Cell 56: 1019-1032 (1989)).

In one embodiment of the invention, the basic peptide comprises amino acids 47-57 of the HIV-1 TAT peptide. In another embodiment, the basic peptide comprises amino acids 48-60 of the HIV-1 TAT peptide. In still another embodiment, the basic peptide comprises amino acids 49-57 of the HIV-1 TAT peptide. In yet another embodiment, the basic peptide comprises amino acids 49-57, 48-60, or 47-57 of the HIV-1 TAT peptide, does not comprise amino acids 22-36 of the HIV-1 TAT peptide, and does not comprise amino acids 73-86 of the HIV-1 TAT peptide. In still another embodiment, the specific peptides set forth in Table 1, below, may be used as carrier peptides in the methods and compositions of the invention.

TABLE 1

| Peptide | Sequence | SEQ ID NO: |
|---|---|---|
| HIV-1 TAT (49-57) | RKKRRQRRR | 20 |
| HIV-1 TAT (48-60) | GRKKRRQRRRTPQ | 21 |
| HIV-1 TAT (47-57) | YGRKKRRQRRR | 22 |
| Kaposi fibroblast growth factor | AAV ALL PAV LLA LLA P + VQR KRQ KLMP | 23 |
| of caiman crocodylus Ig(5) light chain | MGL GLH LLV LAA ALQ GA | 24 |
| HIV envelope glycoprotein gp41 | GAL FLG FLG AAG STM GA + PKS KRK (NLS of the SV40) | 25 |
| Drosophila Antennapedia | RQI KIW FQN RRM KWK K amide | 26 |
| RGD peptide | X-RGD-X | 27 |
| influenza virus hemagglutinin envelop glycoprotein | GLFEAIAGFIENGWE GMIDGGGYC | 28 |
| transportan A | GWT LNS AGY LLG KIN LKA LAA LAK KIL | 29 |
| Pre-S-peptide | (S)DH QLN PAF | 30 |
| Somatostatin (tyr-3-octreotate) | (S)FC YWK TCT | 31 |

(s) optional Serine for coupling
italic = optional D isomer for stability

Other arginine rich basic peptides are also included in the present invention. For example, a TAT analog comprising D-amino acid- and arginine-substituted TAT(47-60), RNA-binding peptides derived from virus proteins such as HIV-1 Rev, and flock house virus coat proteins, and the DNA binding sequences of leucine zipper proteins, such as cancer-related proteins c-Fos and c-Jun and the yeast transcription factor GCN4, all of which contain several arginine residues (see Futaki, et al. (2001) *J. Biol Chem* 276(8):5836-5840 and Futaki, S. (2002) *Int J. Pharm* 245(1-2):1-7, which are incorporated herein by reference). In one embodiment, the arginine rich peptide contains about 4 to about 11 arginine residues. In another embodiment, the arginine residues are contiguous residues.

Subunits other than amino acids may also be selected for use in forming transport polymers. Such subunits may include, but are not limited to hydroxy amino acids, N-methyl-amino acids amino aldehydes, and the like, which result in polymers with reduced peptide bonds. Other subunit types can be used, depending on the nature of the selected backbone.

A variety of backbone types can be used to order and position the sidechain guanidino and/or amidino moieties, such as alkyl backbone moieties joined by thioethers or sulfonyl groups, hydroxy acid esters (equivalent to replacing amide linkages with ester linkages), replacing the alpha carbon with nitrogen to form an aza analog, alkyl backbone moieties joined by carbamate groups, polyethyleneimines (PEIs), and amino aldehydes, which result in polymers composed of secondary amines.

A more detailed backbone list includes N-substituted amide (CONR replaces CONH linkages), esters ($CO_2$), ketomethylene ($COCH_2$) reduced or methyleneamino ($CH_2NH$), thioamide (CSNH), phosphinate ($PO_2RCH_2$), phosphonamidate and phosphonamidate ester ($PO_2RNH$), retropeptide (NHCO), transalkene (CR.dbd.CH), fluoroalkene (CF.dbd.CH), dimethylene ($CH_2 2CH_2$), thioether ($CH_2S$), hydroxyethylene ($CH(OH)CH_2$), methyleneoxy ($CH_2O$), tetrazole (CN24), retrothioamide (NHCS), retroreduced ($NHCH_2$), sulfonamido ($SO_2NH$), methylenesulfonamido ($CHRSO_2NH$), retrosulfonamide ($NHSO_2$), and peptoids (N-substituted glycines), and backbones with malonate and/or gem-diaminoalkyl subunits, for example, as reviewed by Fletcher et al. (1998) and detailed by references cited therein. Peptoid backbones (N-substituted glycines) can also be used. Many of the foregoing substitutions result in approximately isosteric polymer backbones relative to backbones formed from α-amino acids.

Polymers are constructed by any method known in the art. Exemplary peptide polymers can be produced synthetically, preferably using a peptide synthesizer (Applied Biosystems Model 433) or can be synthesized recombinantly by methods well known in the art.

N-methyl and hydroxy-amino acids can be substituted for conventional amino acids in solid phase peptide synthesis. However, production of polymers with reduced peptide bonds requires synthesis of the dimer of amino acids containing the reduced peptide bond. Such dimers are incorporated into polymers using standard solid phase synthesis procedures. Other synthesis procedures are well known in the art.

In one embodiment of the invention, an RNA interfering agent and the carrier polymer are combined together prior to contacting a biological membrane. Combining the RNA interfering agent and the carrier polymer results in a association of the agent and the carrier. In one embodiment, the RNA interfering agent and the carrier polymer are not indirectly or directly linked together, e.g., either covalently or chemically. Therefore, linkers are not required for the formation of the duplex. In another embodiment, the RNA interfering agent and the carrier polymer are bound together via electrostatic bonding.

It is known that depending upon the expression vector and transfection technique used, only a small fraction of cells may effectively uptake the siRNA molecule. In order to identify and select these cells, antibodies against a cellular target can be used to determine transfection efficiency through immunofluorescence. Preferred cellular targets include those which are present in the host cell type and whose expression is relatively constant, such as Lamin A/C. Alternatively, co-transfection with a plasmid containing a cellular marker, such as a CMV-driven EGFP-expression plasmid, luciferase, metalloprotease, BirA, β-galactosidase and the like may also be used to assess transfection efficiency. Cells which have been transfected with the siRNA molecules can then be identified by routine techniques such as immunofluorescence, phase contrast microscopy and fluorescence microscopy.

Depending on the abundance and the life time (or turnover) of the targeted protein, a knock-down phenotype may become apparent after 1 to 3 days, or even later. In cases where no phenotype is observed, depletion of the protein may be observed by immunofluorescence or Western blotting. If the protein is still abundant after 3 days, cells can be split and transferred to a fresh 24-well plate for re-transfection.

If no knock-down of the targeted protein is observed, it may be desirable to analyze whether the target mRNA was effectively destroyed by the transfected siRNA duplex. Two days after transfection, total RNA can be prepared, reverse transcribed using a target-specific primer, and PCR-amplified with a primer pair covering at least one exon-exon junction in order to control for amplification of pre-mRNAs. RT/PCR of a non-targeted mRNA is also needed as control. Effective depletion of the mRNA yet undetectable reduction of target protein may indicate that a large reservoir of stable protein may exist in the cell. Multiple transfection in sufficiently long intervals may be necessary until the target protein is finally depleted to a point where a phenotype may become apparent.

RNA interfering agents of the instant invention also include, for example, small molecules which interfere with or inhibit expression of a target gene. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The dose of the particular RNA interfering agent, e.g., an siRNA or a small molecule, will be in an amount necessary to effect RNA interference, e.g., post translational gene silencing (PTGS) of the particular target gene, thereby leading to inhibition of target gene expression or inhibition of activity or level of the protein encoded by the target gene. Assays to determine expression of the target gene, e.g., CCR5 or p24, and the activity or level of the protein encoded by the target gene, are known in the art. For example, reduced levels of target gene mRNA may be measured by in situ hybridization (Montgomery et al., (1998) *PNAS USA* 95:15502-15507) or Northern blot analysis (Ngo, et al. (1998) *PNAS USA* 95:14687-14692).

III. Methods of Treatment:

The present invention provides for both prophylactic and therapeutic methods of treating a subject at risk of (or susceptible to) an infectious disease or disorder, including, but not limited to HIV, AIDS, and an AIDS-related disease or disorder. As used herein, "treatment," or "treating," is defined as the application or administration of a therapeutic agent (e.g., one or more RNA interfering agents, e.g., siRNAs) to a patient, or application or administration of a therapeutic agent to an isolated tissue or cell line from a patient with the purpose to cure, heal, alleviate, relieve, alter, remedy, ameliorate, improve or affect the infectious disease or disorder, symptoms of an infectious disease or disorder, or inoculate against an infectious agent which is capable of causing an infectious disease or disorder.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with one or more siRNAs according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, an infectious disease or disorder, by administering to the subject one or more therapeutic agents, e.g., the RNA interfering agents as described herein. For example, the RNA interfering agents described herein may be used as microbicides to substantially reduce transmission of diseases transmitted by microbes, such as, for example, sexually transmitted infections (STIs), e.g., hepatitis, e.g., HBV, HCV, HGV, human papilloma virus (HPV), herpes (HSV-2), other viral infections, and/or bacterial infections. Subjects at risk for an infectious disease or disorder, can be identified by, for example, any known risk factors for an infectious disease or disorder.

Administration of a prophylactic agent can occur prior to the manifestation of symptoms characteristic of an infectious disease or disorder, such that the infectious disease or disorder is prevented or, alternatively, delayed in its progression. Any mode of administration of the therapeutic agents of the invention, as described herein or as known in the art, including topical administration of the RNA interfering agents of the instant invention, may be utilized for the prophylactic treatment of an infectious disease or disorder.

Formulations of the active compounds as described herein (e.g., an RNA interfering agent, e.g., an siRNA) may be administered to a subject at risk for an RNA interfering agent-mediated disease or disorder, e.g., a viral or bacterial disease or disorder, such as, for example, HIV, or another sexually transmitted disease or infection, or any other infectious agent, e.g., a virus, as a topically applied prophylactic, e.g. for administration on mucosal membranes, e.g., orally, vaginally, or rectally, or topically to epithelia, to prevent transmission of a viral or bacterial disease or disorder, such as, for example, HIV or another sexually transmitted disease or infection. In one embodiment, the compositions comprising the RNA interfering agent and the carrier polymer may be administered prior to exposure to the infectious agent. In vitro experiments illustrate that the antiviral state induced by introduced duplex siRNAs can last for weeks. Therefore, in one embodiment, an siRNA-based microbicide need not be applied before each sexual encounter. Accordingly, in another embodiment, the prophylactic effect of the RNA interfering agent, e.g., the siRNA, is prolonged, e.g. lasts for at least one week, preferably two or more weeks. In another embodiment, the compositions comprising the RNA interfering agent may be administered, e.g., topically, at intervals, e.g., one or more times per week, or one or more times per month, rather than directly prior to exposure to an infectious agent.

For example, the therapeutic agents described herein may be formulated as a spray, lotion, cream, foam, gel, and the like, or any other suitable delivery method known in the art or described herein, and may include, for example, standard lubricants and/or detergents or other additives. In one embodiment, these formulations are administered in combination with barrier methods for protection against sexually transmitted diseases, or may be applied to condoms or other barrier protection devices.

The topically applied agents may also be used in combination with a spermicidal or other microbicidal agent as described in, for example, U.S. Pat. No. 6,302,108, the entire contents of which are expressly incorporated herein, or in combination with other prophylactic agents for the prevention of HIV or other STDs. The compounds can also be prepared in the form of suppositories (e.g., with conventional suppository bases such as cocoa butter and other glycerides) or retention enemas for rectal delivery.

2. Therapeutic Methods

Another aspect of the invention pertains to methods of modulating gene expression or protein activity, e.g., cellular gene expression or activity and/or expression or activity of a gene or sequence of an infectious agent, e.g., viral gene expression or protein activity in order to treat an infectious disease or disorder. Accordingly, in an exemplary embodiment, the modulatory method of the invention involves contacting a cell with a therapeutic agent (e.g., one or more RNA interfering agents, e.g., siRNAs, e.g., one or more siRNAs targeting a cellular gene or sequence and/or one or more siRNAs targeting a gene or sequence of an infectious agent, e.g., a viral gene or sequence), such that expression of the target gene or genes is prohibited. These methods can be performed in vitro (e.g., by culturing the cell) or, alternatively, in vivo (e.g., by administering the agent to a subject).

One skilled in the art can readily determine the appropriate dose, schedule, and method of administration for the exact formulation of the composition being used, in order to achieve the desired "effective level" in the individual patient. One skilled in the art also can readily determine and use an appropriate indicator of the "effective level" of the compounds of the present invention by a direct (e.g. analytical chemical analysis) or indirect (e.g., with surrogate indicators of viral infection), or analysis of appropriate patient samples (e.g., blood and/or tissues).

The therapeutic compositions of the invention can also be administered to cells ex vivo, e.g., cells are removed from the subject, the compositions comprising the siRNAs of the invention are administered to the cells, and the cells are reintroduced into the subject by, e.g., transplantation or grafting. Cells can also be used which are obtained from a donor (i.e., a source other than the ultimate recipient), and applied to a recipient by, e.g., transplanting or grafting, subsequent to administration of the siRNAs of the invention to the cells. Vectors, e.g., gene therapy vectors, can be used to deliver the therapeutic agents to the cells.

The prophylactic or therapeutic pharmaceutical compositions of the invention can contain other pharmaceuticals, in conjunction with a vector according to the invention, when used to therapeutically treat or prevent an infectious disease or disorder and can also be administered in combination with other pharmaceuticals used to treat or prevent an infectious disease or disorder. For example, in the case of HIV, the prophylactic or therapeutic pharmaceutical compositions of the invention can also be used in combination with other pharmaceuticals which modulate the expression or activity of chemokine receptors, e.g., CCRs and CXC receptors. Examples of pharmaceuticals used to treat or prevent an infectious disease or disorder, e.g., HIV infection, AIDS, and AIDS-related diseases include, without limitation, antiretroviral therapies, e.g., protease inhibitors, immunomodulators, immunostimulants, antibiotics, antiprotozoal agents, antifungal agents, antiviral compounds, anticancer drugs, and other agents and treatments, or combinations thereof, that can be employed to treat or prevent an infectious disease or disorder, e.g., HIV infection, AIDS, and AIDS-related diseases or delay the progression thereof. Specific pharmaceuticals which may be used in combination with the siRNAs of the invention to treat or prevent HIV infection, AIDS, and AIDS-related diseases include, without limitation, Nevirapine, Efavirenz, Delavirdine, Zidovudine, Didanosine, Zalcitabine, Stavudine, Lamivudine, Abacavir, Lamivudine+Zidovudine, Saquinavir, Ritonavir, Indinavir, Nelfinavir, Amprenavir, Lopinavir+Ritonavir, Azithromycin, Clarithromycin, Clindamycin; Ceftriaxone, Cefixime, Ciprofloxacin; Rifabutin, Trimethoprim/Sulphamethoxazole (IV); Pentamidine, Pyrimethamine, Sulfadiazine, Folinic acid, Acyclovir, Cidofovir, Ganciclovir, Forscarnet, Amphotericin B, Fluconazole, Itraconazole, Ketoconazole; Vinblastine, Etoposide, Bleomycin, and Vincristine.

3. Pharmacogenomics

The therapeutic agents as described herein (e.g., an RNA interfering agent, e.g., an siRNA, e.g., one or more siRNAs targeting a cellular gene or sequence and/or one or more siRNAs targeting a gene or sequence of an infectious agent) can be administered to individuals to treat (prophylactically or therapeutically) an infectious disease or disorder, e.g., HIV, AIDS, and an AIDS-related disease or disorder. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer one or more therapeutic agents as described herein (e.g. an RNA interfering agent, e.g., an infectious disease or disorder) as well as tailoring the dosage and/or therapeutic regimen of treatment with an siRNA, e.g., an infectious disease or disorder.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11): 983-985 and Linder, M. W. et al. (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug target is known, all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing. enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a therapeutic agents as described herein (e.g., an RNA interfering agent, e.g. an siRNA, such as a CCR5 siRNA, a p24 siRNA, or a combination of both).

IV. Pharmaceutical Compositions

The RNA interfering agents, e.g., the siRNAs of the invention, can be incorporated into pharmaceutical compositions suitable for administration. Such compositions typically comprise one or more RNA interfering agents, e.g., siRNAs, such as one or more siRNA targeting a cellular gene or sequence, e.g., a CCR5 siRNA, and/or, one or more siRNA targeting a gene or sequence of an infectious agent, e.g., a p24 siRNA, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, vaginal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Formulations of the active compounds as described herein (e.g. an RNA interfering agent, e.g., an siRNA, e.g., an infectious disease or disorder) may be administered to a subject at risk for microbial infection as a topically applied prophylactic, e.g., for administration on mucosal membranes, e.g., vaginally, or rectally, to prevent sexual transmission of HIV or other sexually transmitted infections.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to macrophages containing, for example, phosphatidylserine) can also be used as pharmaceutically acceptable carriers. These can be prepared according to methods known to those skilled in the art, for example, as described in U.S. Pat. No. 4,522,811 U.S. Pat. No. 5,643,599, the entire contents of which are incorporated herein. Alternatively, the therapeutic agents of the invention may be prepared by adding a poly-G tail to one or more ends of the siRNA for uptake into target cells, e.g., macrophages or CD4 T cells. Moreover, siRNA may be fluoro-derivatized and delivered to the target cell as described by Capodici, et al. (2002) J. Immuno. 169(9):5196.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the siRNA in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an RNA interfering agent (i.e., an effective dosage) ranges from about 0.001 to 3,000 mg/kg body weight, preferably about 0.01 to 2500 mg/kg body weight, more preferably about 0.1 to 2000, about 0.1 to 1000 mg/kg body weight, 0.1 to 500 mg/kg body weight, 0.1 to 100 mg/kg body weight, 0.1 to 50 mg/kg body weight, 0.1 to 25 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNA interfering agent can include a single treatment or can include a series of treatments.

In a preferred example, a subject is treated with an RNA interfering agent in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. In another embodiment, a subject is treated one time every week, one time every two weeks, one time per every three weeks, or one time per every four or more weeks. It will also be appreciated that the effective dosage of an RNA interfering agent used for treatment may increase or decrease over the course of a particular treatment. Changes in dosage may result and become apparent from the results of diagnostic assays as described herein.

It is understood that appropriate doses of RNA interfering agents, e.g., siRNAs, depends upon a number of factors within the ken of the ordinarily skilled physician, veterinarian, or researcher. The dose(s) of the siRNA will vary, for example, depending upon the identity, size, and condition of the subject or sample being treated, further depending upon the route by which the composition is to be administered, if applicable, and the effect which the practitioner desires the RNA interfering agent, e.g. siRNA, to have upon the target gene, e.g., the cellular gene or sequence and/or the a gene or sequence of an infectious agent.

Exemplary doses include milligram or microgram amounts of the an RNA interfering agent per kilogram of subject or sample weight (e.g., about 1 microgram per kilogram to about 5,000 milligrams per kilogram, about 500 micrograms per kilogram to about 5 milligrams per kilogram, about 100 micrograms per kilogram to about 5 milligrams per kilogram, or about 1 microgram per kilogram to about 50 micrograms per kilogram.

The siRNA molecules of the invention can be inserted into vectors as described herein and known in the art. These constructs can be delivered to a subject by, for example, intravenous injection, local administration (see U.S. Pat. No. 5,328, 470) or by stereotactic injection (see e.g., Chen et al. (1994) Proc. Natl. Acad. Sci. USA 91:3054-3057). The pharmaceutical preparation of the siRNA vector can include the siRNA vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

This invention is further illustrated by the following examples which should not be construed as limiting. The contents of all references, patents and published patent applications cited throughout this application, as well as the Figures and Sequence Listing, are incorporated herein by reference.

EXAMPLES

Example 1

Sustained siRNA-Mediated HIV Inhibition in Primary Macrophages

Synthetic 21-23 nucleotide siRNA duplexes suppress HIV replication in human cell lines and activated $CD4^-T$ cells (Jacque, J. M., et al. (2002) Nature 418, 435-8; Coburn, G. A. & Cullen, B. R. (2002) J. Virol 76, 9225-31; Novina, C. D. et al. (2002) Nat Med 8, 681-6; Lee, N. S. et al. (2002) Nat Biotechnol 20, 500-5). However, the silencing effect of siRNAs in these actively replicating cells peaks around 96 hours, but tapers off thereafter and is completely lost by day 9 (Novina, C. D. et al. (2002) Nat Med 8, 681-6; Tuschl, T. (2002) Nat Biotechnol 20, 446-8), presumably because of siRNA dilution with cell division or degradation inside the cell (Ullu, E., et al. (2002) Philos Trans R Soc Lond B Biol Sci 357, 65-70). Macrophages are terminally differentiated, non-dividing cells that constitute a significant reservoir for HIV-1 in vivo (Sherman, M. P. & Greene, W. C. (2002) Microbes Infect 4, 67-73; Meltzer, M. S. et al. (1990) Annu Rev Immunol 8, 169-94). They are also relatively immune to the cytopathic effects of HIV and survive for long periods after infection (Castro, B. A., et al. (1998) Aids 2 Suppl 1, S17-27). Thus, it was investigated whether more sustained siRNA-mediated viral silencing could be achieved in monocyte-derived macrophages (MDMs).

Figure 1B:
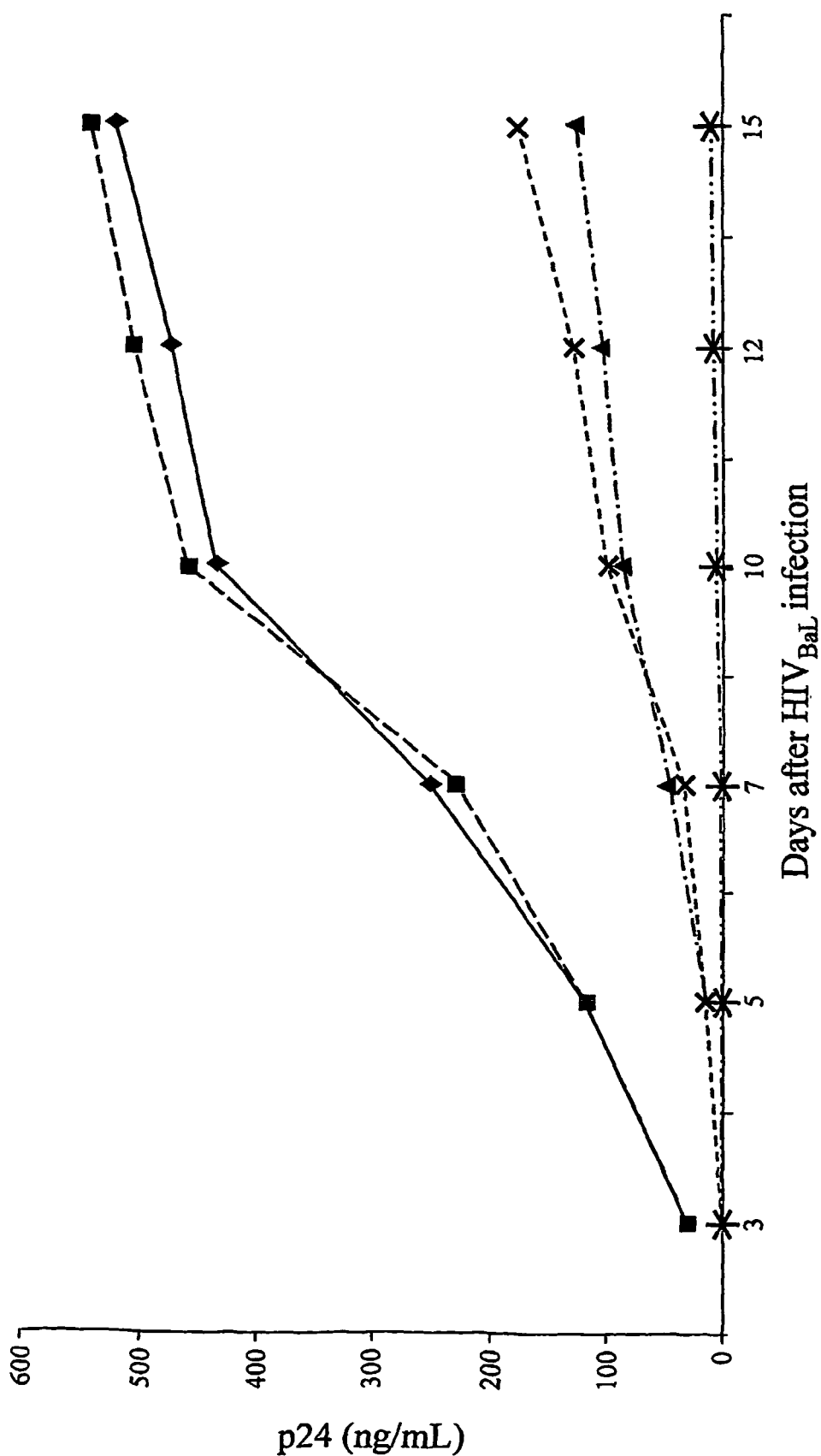
Figure 1C:
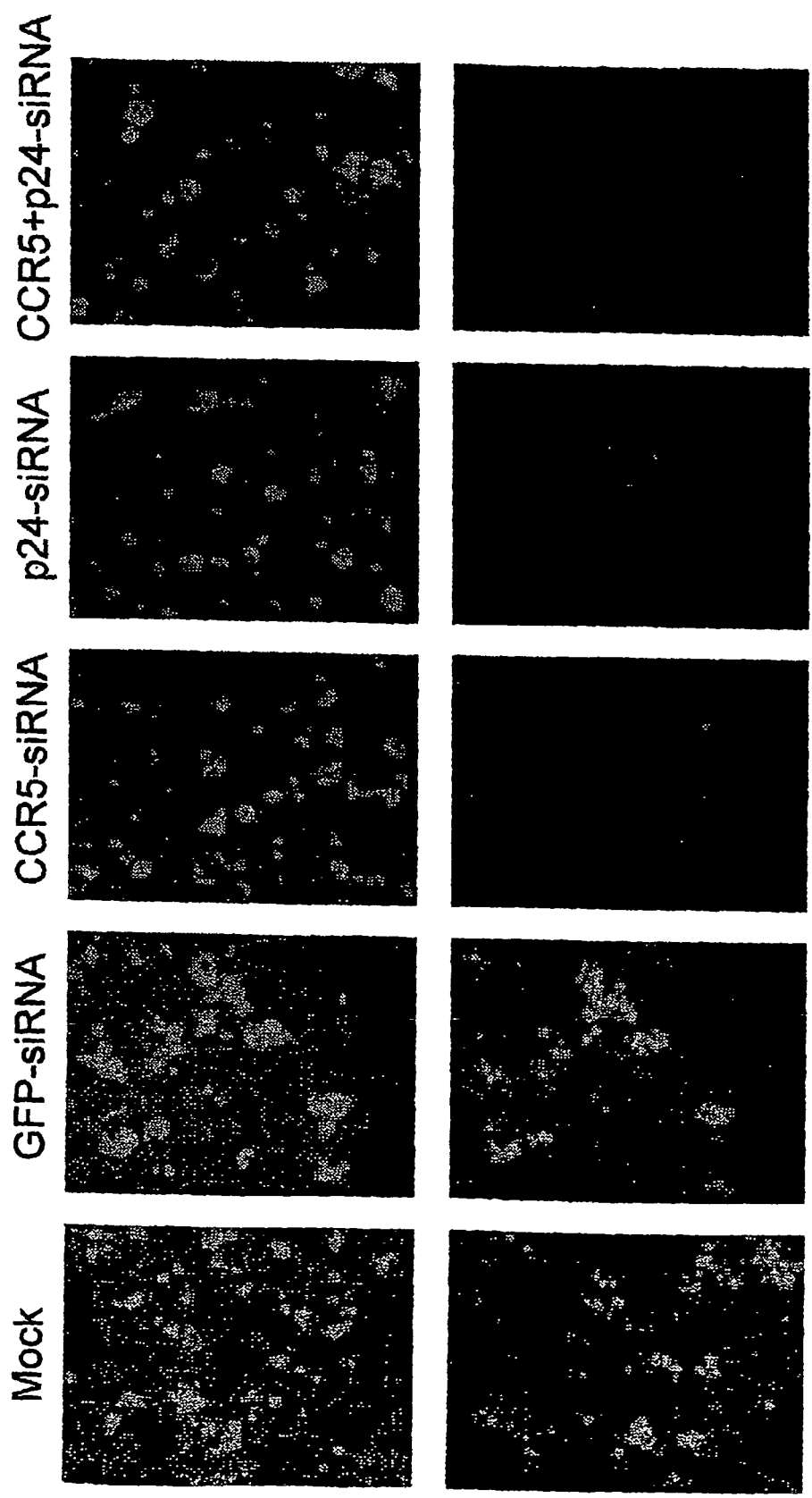
Figure 1D:
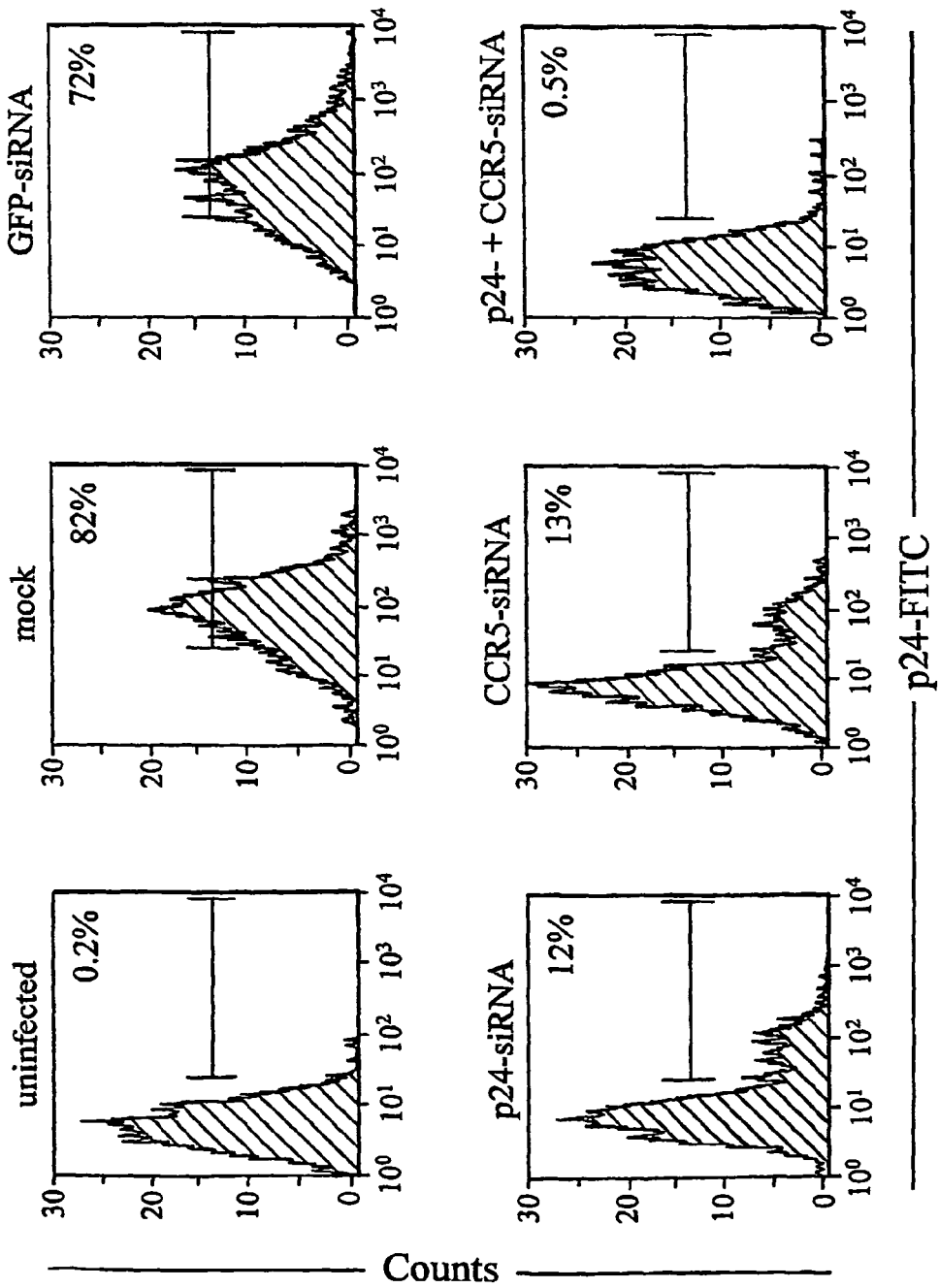

Previous reports on siRNA-directed protection against HIV-1 have targeted viral genes (Jacque, J. M., et al. (2002) Nature 418, 435-8; Coburn, G. A. & Cullen, B. R. (2002) J Virol 76, 9225-31; Novina, C. D. et al. (2002) Nat Med 8, 681-6) or targeted the cellular receptor CD4 (Novina, C. D. et al. (2002) Nat Med 8, 681-6). However, CD4 targeting may not be a feasible approach because of its importance in immune function. On the other hand, CCR5, the major HIV coreceptor for viral entry into macrophages, may be a better cellular target since a 32 bp homozygous deletion of the gene, which abrogates function, has no deleterious immunological consequences (Nansen, A. et al. (2002) Blood 99, 1237-45) but provides protection from HIV infection (Liu, R. et al. (1996) Cell 86, 367-77; Samson, M. et al. (1996) Nature 382, 722-5). Thus, to determine anti-HIV effects of siRNA in macrophages, the CCR5 and the viral p24 genes were targeted. First, it was verified that MDMs are susceptible to siRNA delivery by transfecting with Cy5-labeled p24 siRNA. After 24 hours of transfection, 84% of CD 14+ macrophages were Cy5+ by flow cytometry (FIG. 1a), a transfection efficiency comparable to that observed with HeLa cells (~90%). The siRNA was not taken up by non-specific phagocytosis because, in the absence of oligofectamine, <6% of MDMs were Cy5+ (FIG. 1a). To determine anti-viral effects of siRNAs, MDMs were transfected with CCR5 or viral p24 siRNAs singly or in combination, and challenged with R5 (BaL) macrophage tropic virus 2 days later. Periodic measurement of cell-free viral particle production by p24 ELISA of culture supernatants from either CCR5 or p24 siRNA transfected MDMs revealed a 4-6 fold reduction compared to mock and GFP siRNA-transfected controls (FIG. 1b). Furthermore, fluorescent in situ hybridization of the cultures on day 7 after infection revealed a corresponding reduction in HIV RNA in CCR5 or p24 siRNA transfected MDMs (FIG. 1c). Similarly, flow cytometric analysis of p24 expression also demonstrated a 7-fold reduction in p24 expression with CCR5 or p24 siRNA transfection as compared to controls for up to 15 days (FIG. 1d). More importantly, transfection with both siRNAs was able to abrogate HIV infection throughout the 15-day period of observation (FIGS. 1b and 1d). Combined treatment of p24 and CCR5 siRNA was synergistic and completely abrogated viral infection, due most likely to interruption of 2 steps in the viral life cycle, with CCR5 siRNA blocking viral entry and p24 siRNA destroying the virus slipping through the remaining coreceptors or taken up passively. Thus, siRNAs can provide lasting protection against HIV in macrophages.

These results suggest a role for siRNA for potential preventive strategy. To realize this potential, it may be important that siRNAs persist in the cells for long periods of time before infection. However, it will be understood that little or no induction or persistence of siRNA in affected membranes is necessary to block sexual transmission of infectious agents.

Figure 2A:
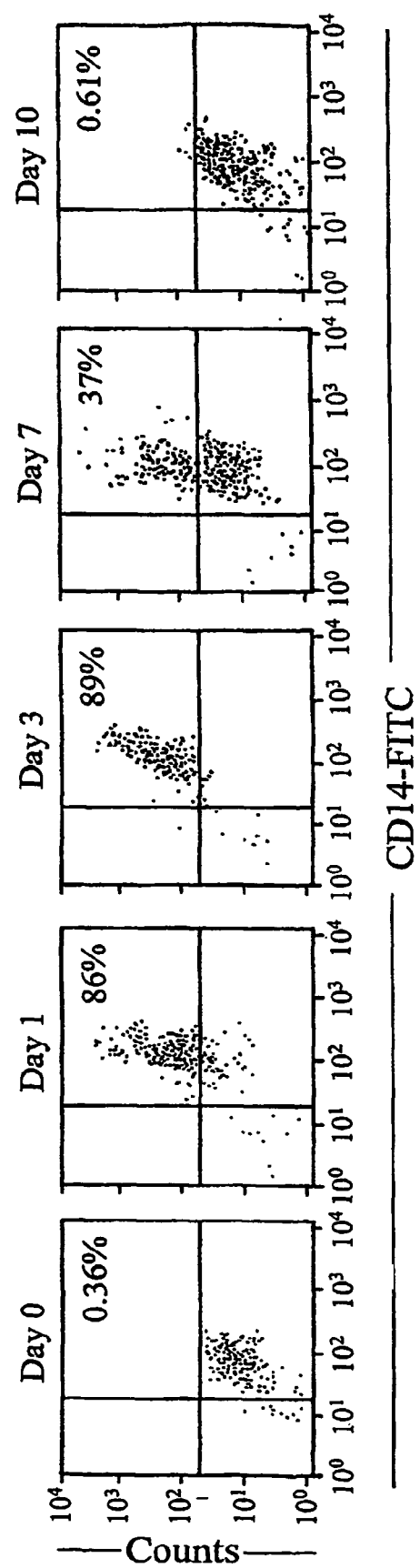
FIG. 2. CCR5-, but not p24 siRNA confers sustained and uniform protection when MDMs are infected at increasing intervals after transfection. a. MDMs were transfected with Cy5-labeled p24 siRNA and Cy5 fluorescence was measured at indicated days. b. GFP- or CCR5 siRNA-transfected MDMs were examined for CCR5 expression over time. Overlay histograms of CCR5 staining of mock transfected cells (open) and siRNA-transfected cells (filled) are shown. c. RT-PCR for CCR5 and β actin mRNA expression in mock transfected (lanes 2-5) and CCR5-siRNA transfected cells (lanes 6-9) on day 1 (lanes 2 and 6), day 4 (lanes 3 and 7), day 7 (lanes 4 and 8) and day 15 (lanes 5 and 9) after transfection (M: molecular 12 weight marker; lane 1: negative control). d. MDMs were transfected with GFP-(upper panel), p24– (middle panel) or CCR5 (lower panel) siRNA and infected with $HIB_{BaL}$ at indicated times after transfection. Cells were analyzed 10 days post-infection for p24 expression by flow cytometry. Percentage of p24+ cells is shown in each panel.
Figure 2B:
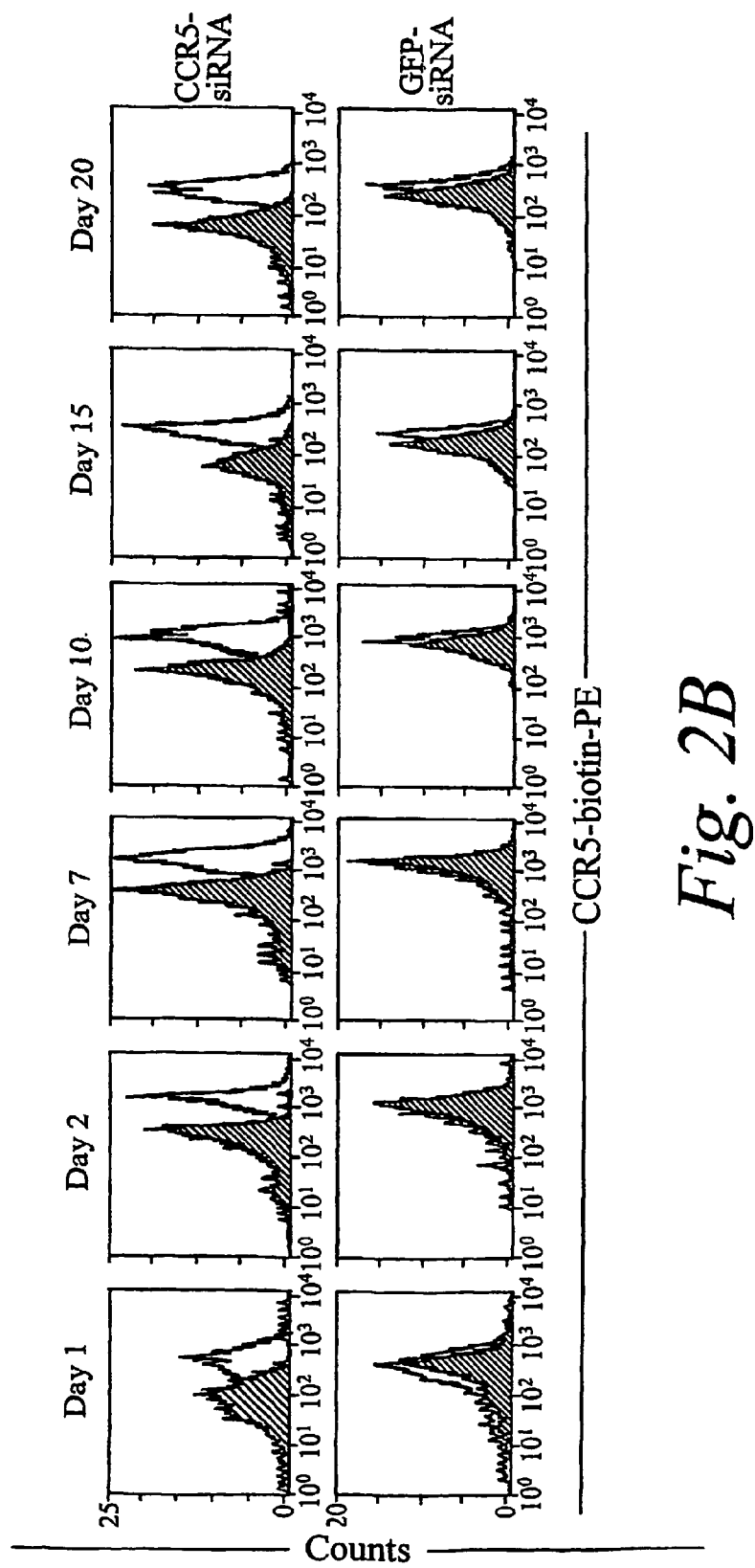
Figure 2C:
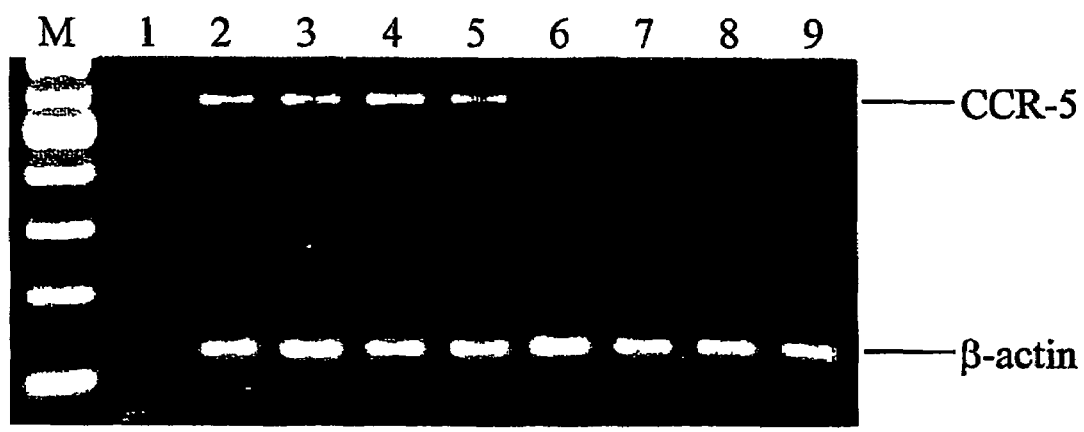
Figure 2D:
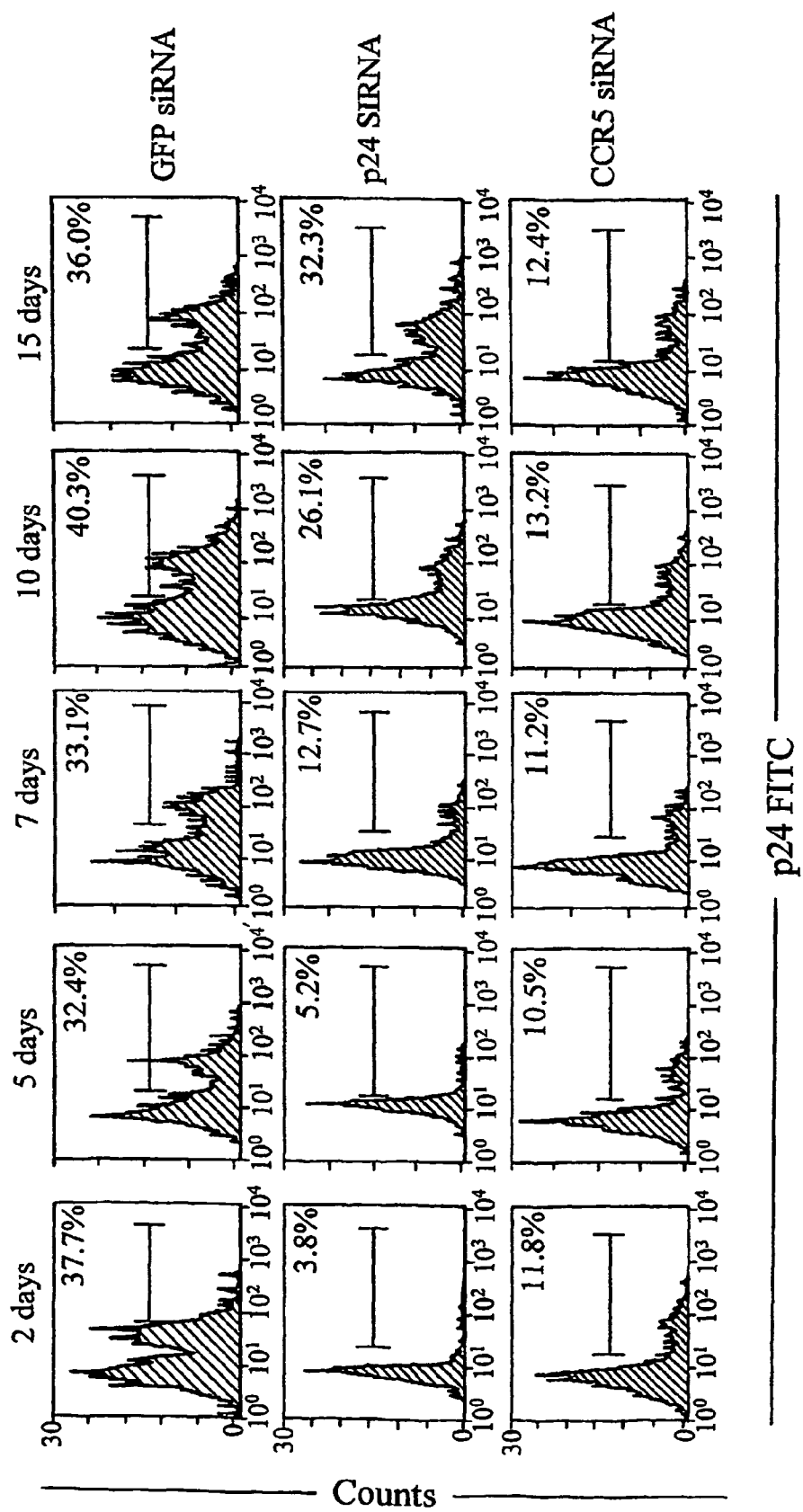

To address the issue of persistence of siRNA in the cells, the longevity of tansfected Cy5-labeled p24 siRNA and CCR5 siRNA-mediated suppression of endogenous CCR5 expression in uninfected MDMs was determined. The levels of intracellular Cy5-p24 siRNA in uninfected MDMs, measured by flow cytometry, gradually declined with time and were undetectable 10 days after transfection (FIG. 2a). In contrast, CCR5 expression in CCR5 siRNA transfected cells remained uniformly silenced from 1-20 days after transfection (FIG. 2b). CCR5 mRNA was also completely silenced as revealed by highly sensitive RT-PCR analysis of the samples on day 1, 4, 7 and 15 after CCR5 siRNA transfection (FIG. 2c). CCR5 mRNA was not detected in these cultures even after an additional 25 cycles of amplification. To test if these differences in intracellular survival are also reflected in HIV suppression, MDMs were transfected with CCR5 or p24 siRNA and initiated infections at increasing intervals after transfection, measuring p24 levels 10 days after infection. Consistent with long term suppression of CCR5 expression, compared to control GFP siRNA, CCR5 siRNA provided equivalent protection whether the cells were infected 2 or 15 days after transfection (FIG. 1d). On the other hand, p24 siRNA provided maximal protection when the cells were infected within 5 days after transfection but showed a declining level of protection when the interval between transfection and infection was extended further. The reason for the differential longevity of siRNAs targeting cellular versus viral gene is not entirely clear. While not intending to be bound by theory, while the cellular genes are continuously transcribed, providing a substrate for siRNA, viral RNA is available only after infection. The differential effects of targeting cellular and viral genes in non-dividing MDMs, together with the fact that Cy-labeled p24 RNA was only maintained up to 7 days in uninfected cells, suggest that continued presence of the substrate RNA may be needed for intracellular persistence of siRNA. This hypothesis is further strengthened by these results that p24 siRNA was able to suppress HIV for 15 days when infection was done 2 days after transfection (FIG. 1d). In fact, sustenance by self-propagation of siRNA by siRNA primed-RNA dependent RNA polymerase (RdRP) is well known in C. elegans and drosophila but has not been shown in mammalian cells (Ketting, R. F. et al. (2001) Genes Dev 15, 2654-9; Lipardi, C., et al. (2001) Cell 107, 297-307).

To determine the anti-viral potential of siRNAs in established infection, infected MDMs were infected for 16 days before transfecting with CCR5 or p24 siRNA. Prior to transfection, >90% of MDMs were infected. The suppression of viral replication followed over time after transfection. As expected, CCR5 blockade did not significantly reduce virus replication in this setup. In striking contrast, p24 siRNA was able to reduce viral replication by >90% throughout the 15-day period of observation. These results contrast with the inability of p24siRNA to confer HIV resistance when transfection preceded infection by more than 5 days (FIG. 1d). This long lasting viral suppression can be achieved in MDMs with established infection. Moreover, these results also support the idea that the siRNA effect is sustained in the continued presence of target mRNA.

Collectively, these results demonstrate for the first time the feasibility of RNAi-based therapeutics to achieve long lasting suppression of HIV-1 in a physiologic setup, both to prevent infection and to suppress viral replication in established infection. It is remarkable that a single application of synthetic siRNA was able to afford long lasting protection against HV in MDMs. Macrophages represent a key target of HIV in vivo and although the absolute number of infected macrophages is relatively low compared to CD4 T cells, the unique dynamics of HIV replication in these cells makes them a formidable viral reservoir (Aquaro, S. et al. (2002) Antiviral Res 55, 209-25). Macrophages are relatively immune to the cytopathic effects of HIV and can survive for long periods after infection. They replicate large amounts of virus in sequestered cytoplasmic vacuoles with a plateau of virus production lasting for as long as 60 days (Castro, B. A., et al. (1988) Aids 2 Suppl 1, S17-27). Thus, it is significant that this recalcitrant reservoir cells are particularly amenable for siRNA-mediated viral inhibition.

The differential longevity of RNAi against CCR5 and p24 in uninfected cells and between p24 in uninfected and infected cells suggest that target mRNAs sustain or amplify the input siRNA in mammalian cells. However, the siRNA effect rapidly fades in dividing cell lines even in the presence of target mRNAs (Tuschl, T. (2002) Nat Biotechnol 20, 446-8; Sharp, P. A. & Zamore, P. (2000) Science 287,2431-3; Sharp, P. A. (2001) Genes Dev 15, 485-90; Elbashir, S. M. et al. (2001) Nature 411, 494-8). Whether siRNA dilution with cell division interferes with the possible benefits of target mRNAs or whether siRNAs operate differently in different cell types is not clear. Non-dividing MDMs provide an ideal cell type for such mechanistic studies because of the absence of confounding dilutional effects complicating the analysis.

A single nucleotide substitution in the middle of the targeted sequence can lead to the emergence of mutant virus resistant to RNAi (Gitlin, L., et al. (2002) Nature 418, 430-4). This underscores the importance of targeting highly conserved regions of the viral genome as well as using combinations of siRNAs. Targeted host genes may also be relatively resistant to escape mutations. In vivo delivery by intravenous injection of siRNA has been shown to be feasible in mice (Lewis, D. L., et al. (2002) Nat Genet; McCaffrey, A. P. et al. (2002) Nature 418, 38-9).

Methods

Preparation of Human MDMs. Human monocytes were isolated from buffy coats prepared from normal volunteer donors. Peripheral blood mononuclear cells were prepared by Ficoll-Hypaque (Pharmacia Corporation, Peapack, N.J.) density gradient centrifugation and were seeded at $2 \times 10^6$ cells/ml in 24-well plates in RPMI 1640 medium (BioWhittaker, Inc., Walkersville, Md.) supplemented with 10% heat-inactivated human AB serum (Nabi Boca Raton, Fla.), 50 U/ml penicillin, 50 (µg/ml streptomycin and 2 mM L-glutamine. After 5 days of culture, non-adherent cells were removed by repeated gentle washing with warm medium, and the adherent cells were harvested by tripsinization. Over 95% of the adherent cells obtained with this technique were $CD14^+$ macrophages.

Preparation of siRNAs. All siRNAs, including the Cy5-labeled p24, were synthesized at Dharmacon Research, Lafayette, Colo. The sequences of sense and anti-sense strands of siRNAs were as follows:

```
CCR5,  5'-P.CUCUGCUUCGGUGUCGAAAdTdT-3'    (SEQ ID NO:1)
       (sense),

5'-P.UUUCGACACCGAAGCAGAGdTdT-3'    (SEQ ID NO:2)
       (antisense);

p24,   5'-P.GAUUGUACUGAGAGACAGGCU-3'      (SEQ ID NO:3)
       (sense),

5'-P.CCUGUCUCUCUCAGUACAAUCUU-3'    (SEQ ID NO:4)
       (antisense);

GFP,   5'-P.GGCUACGUCCAGGAGCGCACC-3'      (SEQ ID NO:5)
       (sense),

5'-P.UGCGCUCCUGGACGUAGCCUU-3'      (SEQ ID NO:6)
       (antisense).
```

The RNAs were deprotected and annealed according to the manufacturer's instruction.

Transfection of siRNAs. Macrophages were transfected with oligofectamine (Gibco-Invitrogen, Rockville, Md.) in the presence or absence of 1 nmol siRNA duplex as described. After overnight incubation, the cells were washed and used for further studies.

Flow Cytometry. To test CCR5 expression and HIV-1 infection, MDMs were stained with biotin-conjugated DCCR5 antibody (R&D Systems, Inc., Minneapolis, Minn.) followed by avidin-labled streptavidin-PE (BD Pharmingen, San Diego, Calif.), or FITC-labeled Dp24 Mab (Beckman Coulter, Brea, Calif.) and analyzed by flow cytometry on FACS calibur with CellQuest software (Becton Dickinson, Franklin Lakes, N.J.).

HIV-1 infection. MDMs were infected with R5 BAL strain of HIV-1 using 50 ng of p24 gag antigen per well. At indicated times, HIV-1 replication in infected macrophages was evaluated by flow cytometric analysis of p24 expression, and cell-free viral production was measured by ELISA for p24 antigen in supernatants using the Alliance HIV-1 p24 ELISA Kit (Perkin Elmer Life Science Inc., Boston, Mass.).

In situ Hybridization. Infected macrophages cultured in slide chambers were evaluated for HIV-1 mRNA expression using the ViroTect™ HIV-Cell Detection System (Invirion Inc., Frankfurt, Mich.). Cells were fixed, permeabilized and hybridized with FITC-labeled gagpol oligonucleotide probe cocktail as per the manufacturer's protocol. The cells were stained with Texas Red-X Phalloidin (Molecular Probe Inc., Eugene, Oreg.) and analyzed by epifluorescence microscopy. The fluorochromes were independently recorded at excitation wavelengths of 494 and 591 nm.

RT-PCR. cDNA was synthesized from total RNA purified from macrophage cultures at indicated times using the Taq-Man reverse transcription kit (Applied Biosystems, Foster City, Calif.). Aliquots of cDNA were PCR amplified for CCR5 using 5'-ATGGATTATCAAGTGTCAAGTCC-3' (SEQ ID NO:7) and 5'-CCAGAATTGATACTGACTG-TATGG-3' (SEQ ID NO:8) primer pair and for γ actin using 5'-TCTGTCAGGGTTGGAAAGTC-3' (SEQ ID NO:9) and 5'-AAATGCAAACCGCTTCCAAC-3' (SEQ ID NO:10) primer pair. Amplified PCR products were visualized on 1.2% agarose gels.

Example 2

Development of an HIV Microbicide

Heterosexual transmission is the leading cause of new HIV infections worldwide, with transmission from males to females occurring much more efficiently than vice versa. Sexual transmission of HIV occurs when cell-free or cell-associated virus infects cells primarily via the CCR5 co-receptor expressed on macrophages, dendritic cells (DC) and activated T lymphocytes (Alkhatib G, et al. (1996) *Science,* 272, 1955-1958; Huang Y, et al. (1996). *Nat Med,* 2, 1240-1243; Zhu T, et al. (1996). *J Virol,* 70, 3098-3107). In recently infected donors, infection with HIV using the CCR5 co-receptor greatly predominates over CXCR4-using virus (>90%), even when subjects are exposed to both types of virus (Huang Y, et al. (1996). *Nat Med,* 2, 1240-1243; Zhu T, et al. (1996). *J Virol,* 70, 3098-3107). Although semen contains as many as $10^7$ viral particles/ml, the concentration of infectious virus is about 3 logs less (Dyer J R, et al. (1996). *J Virol Methods,* 60, 161-170; Gupta P, et al. (1997). *J Virol,* 71, 6271-6275). Moreover semen levels of infectious virus drop substantially, often to undetectable levels, with HAART (Eron J J, Jr., et al. (2000). *J Infect Dis,* 181, 1622-1628; Barroso P F, et al. (2000). *Ann Intern Med,* 133, 280-284).

Cell-free virus may be more readily transmitted than cell-associated virus (Sodora D L, et al. (1998). *AIDS Res Hum Retroviruses,* 14 Suppl 1, S119-123). Studies with human vaginal and cervical tissue explants suggest that the uninflamed female genital epithelial mucosa provides a tight barrier that prevents transcytosis of cell-free virus or infected lymphocytes (Greenhead P., et al. (2000). *J Virol,* 74, 5577-5586).

Genital epithelial cells are not susceptible to HIV infection. It is likely that the initially infected cell is the Langerhans cell (LC), the resident DC in the stratified squamous epithelium of the vagina and ectocervix. Although early studies of intravaginal application of SIV to rhesus macaques suggested that the earliest infected cells are T cells (Spira, AI, et al. (1996). *J Exp Med,* 183, 215-225; Zhang, Z, et al. (1999). *Science,* 286, 1353-1357), the earliest time point examined was 24 hour post infection, a time at which activated and infected LCs would have migrated out of the epithelium. Infection of LCs has been shown in rhesus macaques exposed to SIV per vagina when looked at earlier time points post infection (Hu J, et al. (2000). *J Virol,* 74, 6087-6095). LCs are also the infected cell in the human epidermal suction blister model of the mucosal epithelium (Kawamura T, et al. (2000). *J Exp Med,* 192, 1491-1500). LCs are immature DCs whose processes extend to the mucosal surface, where they are accessible to HIV infection. They are the gatekeepers of the epithelium, which sample the outside environment and take up foreign antigens including infectious organisms. They are productively infected by HIV, since trypsinization of cell suspensions from these explants, which inactivates cell surface virus, does not affect HIV production in cocultured CD4+T cell blasts. Moreover depletion of LCs from these cultures completely abrogates HIV production. LCs express CCR5, but not DC-SIGN or CXCR4, and in the skin blister model, HIV infection of LCs is CCR5 dependent. It is inhibited by RANTES and anti-CCR5 antibodies, but not by blocking DC-SIGN or CXCR4. Moreover skin explant infection is resistant to viral isolates that use the CXCR4 coreceptor.

Other HIV-susceptible cells, such as macrophages and T cells, are not present in the epidermis and in most instances become infected only from infected LCs. Although some reports have suggested that in cervical tissue culture, T cells are rapidly and directly infected (Collins, K B, et al. (2000). *Nat Med,* 6, 475-479), it is now thought that these results are artifactual consequences of loss of epidermal integrity or leakage around biopsy specimens (Shattock, R J, et al. (2000). *Nat Med,* 6, 607-608). However, sexual transmission is greatly increased in the presence of mucosal inflammation and coinfection with sexually transmitted diseases (del Mar Pujades Rodriguez, M, et al. (2002). *AIDS* 16, 451-462; Grosskurth, H, et al. (2000). *Lancet,* 355, 1981-1987). In vitro activation of T cells in organ cultures also enhances HIV infection. Moreover intravaginal use of the spermicide nonoxynol-9, which cause vaginal inflammation, is associated with an increased risk of transmission, even though in vitro it inhibits HIV infection (van Damme, L, et al. (2002). *Lancet,* 360, 971-977). In addition, thinning of the vaginal and cervical epithelium that occurs in the luteal phase of the menstrual cycle or with exogenous progesterone enhances SIV/SHIV intravaginal transmission (Marx, P A, et al. (1996). *Nat Med,* 2, 1084-1089; Smith, S M, et al. (2000). *J Infect Dis,* 182, 708-715). With coinfection, inflammation, trauma or progesterone, the epithelial barrier is disrupted or thinned, presumably allowing direct infection of subepithelial macrophages and T cells.

Preventing transmission is the best hope for controlling the epidemic. In the absence of an effective vaccine, a microbicide to prevent sexual transmission would make a substantial contribution to controlling spread of HIV. A microbicide for HIV needs to prevent infection of the gatekeeper LCs and not cause inflammation or disruption of the vaginal or cervical epithelium. Ideally the microbicide also inhibits infection of subepithelial macrophages and T cells. Since compliance is a major impediment to microbicide effectiveness, a long acting agent has a great advantage over an agent that needs to be applied just before sexual intercourse. Results indicate that duplex siRNAs can be delivered to macrophages and activated T lymphocytes without transfection and lead to prolonged gene silencing, which can inhibit de novo infection as well as viral replication in already infected cells. These findings indicate that duplex siRNAs is effective as the active component in a microbicide. One of the major barriers for a microbicide is the requirement that it be used just prior to sexual exposure. Because in vitro experiments illustrate that the antiviral state induced by introduced duplex siRNAs can last for weeks, an siRNA-based microbicide need not be applied before each sexual encounter.

Effective Delivery of Duplex siRNA

Effective delivery of siRNAs into cells at risk of infection or infected with HIV is the main obstacle to utilizing RNAi to prevent or treat disease. Current methods for in vitro delivery may not be readily be adapted for in vivo use.

Figure 3:
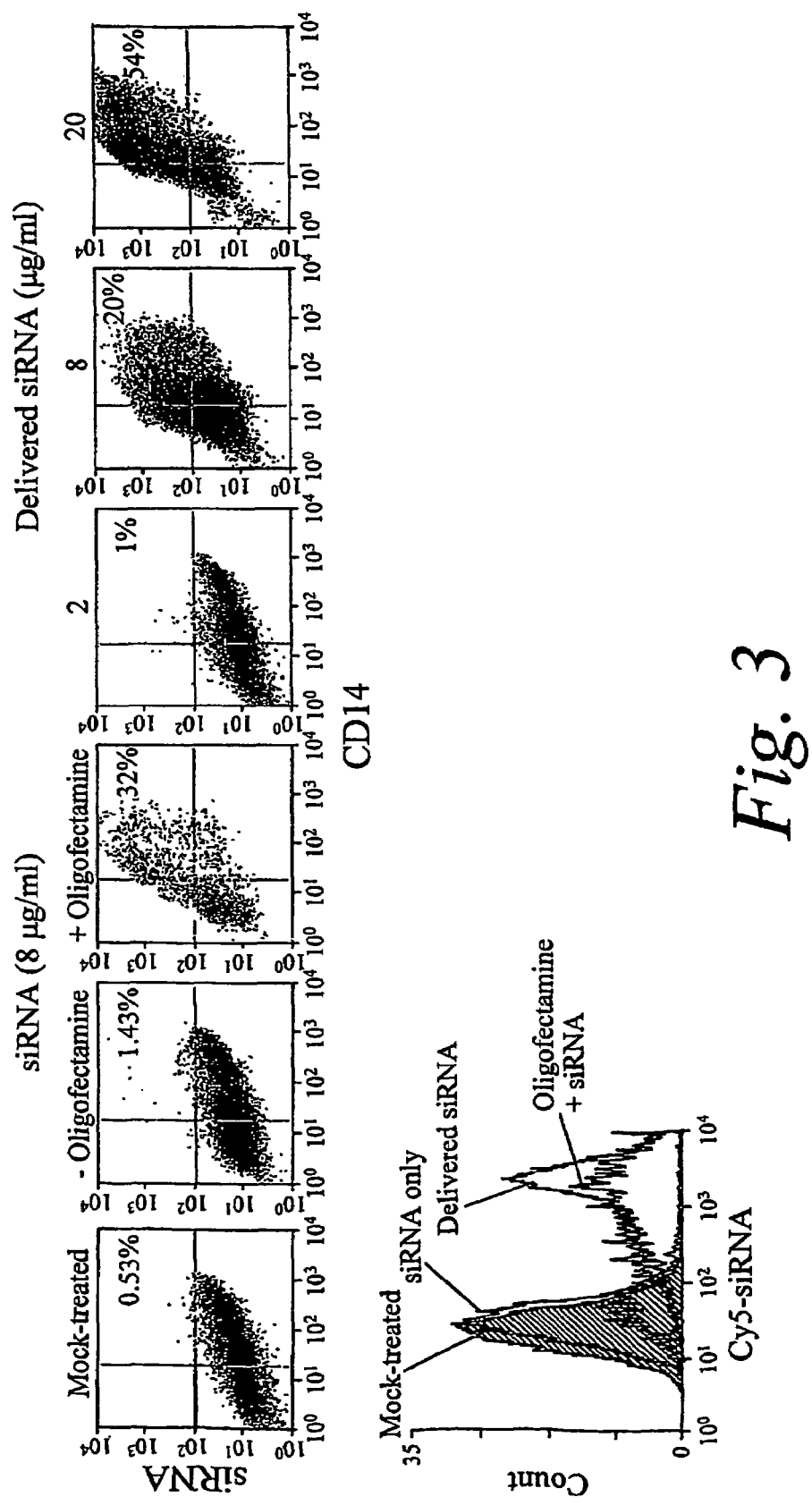
FIG. 3. Duplex siRNA is efficiently delivered to MDMs without transfection. Flourescently labeled siRNA was delivered into human MDMs either by transfection with oligofectamine or by mixing the siRNA with tat peptide. Data are shown as FACs analysis scatter plots vs the macrophage marker, CD14, or by histogram gated on CD 14+ cells.

A delivery method that bypasses transfection and is as efficient as viral transmission itself has been developed. It has been shown that antisense oligonucleotides can be delivered to cells by mixing them with basic peptides, since the basic peptide binds to acidic nucleic acids (Sandgren, S, et al. (2002). *J Biol Chem,* 277, 38877-38883). This same approach has been adapted for introducing siRNAs into cells. Mixing duplex siRNA with a basic peptide derived from HIV tat, known to deliver fusion proteins into the cytosol without activating transcription, efficiently introduces siRNAs into MDMs without transfection (FIG. 3). Utilizing this method, 50% of activated T cells have been transduced. In vivo, intraperitoneal injection of peptide-siRNA duplexes into mice has successfully transduced 30-50% of macrophages.

Figure 4:
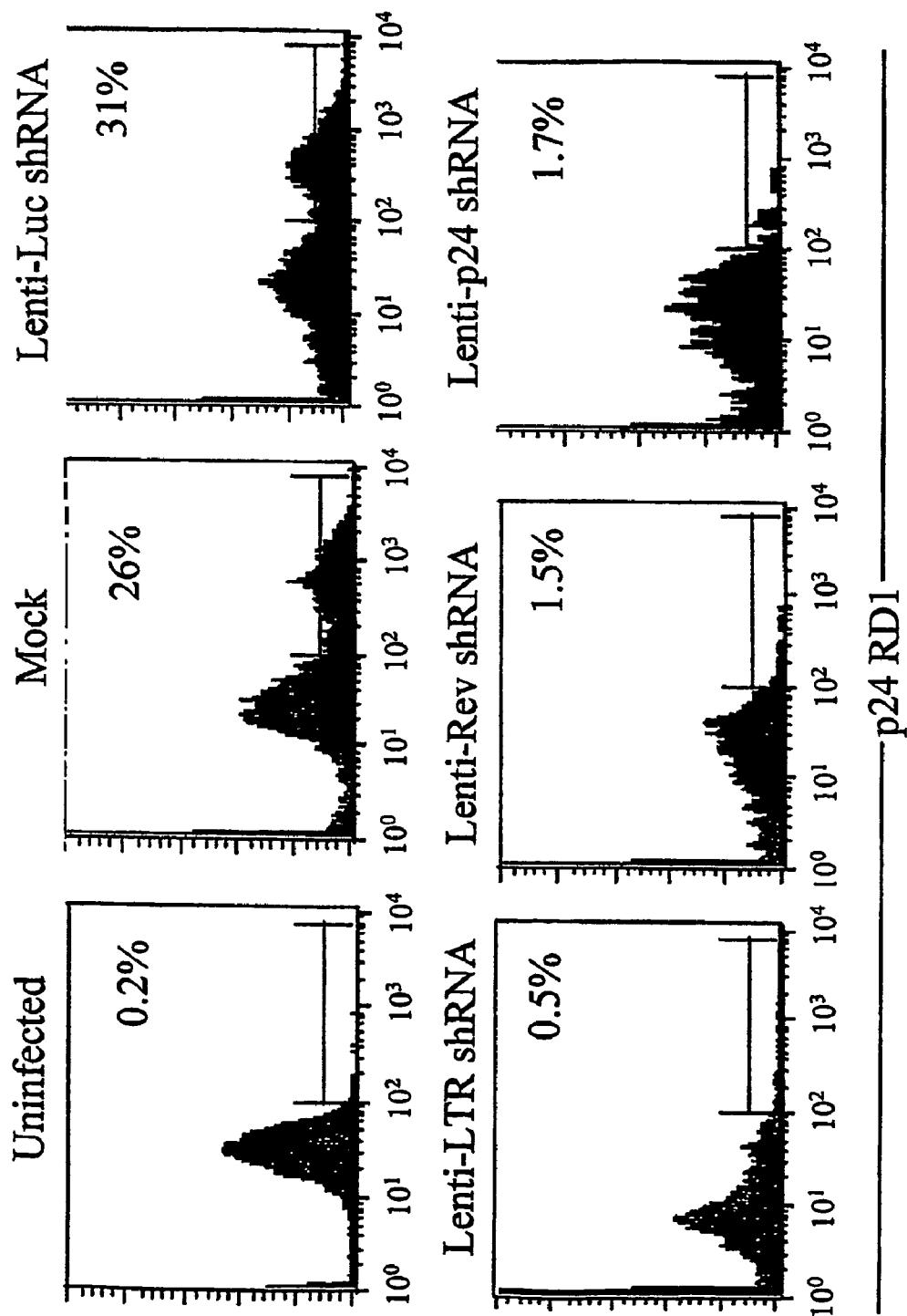
FIG. 4. HIV infection of Primary Cells is Effectively Silenced with Lentivirus Encoding Small Hairpin RNAs (shRNAs). Monocyte-derived macrophages infected with lentivirus encoding shRNAs targeting HIV LTR, rev and gag p24 sequences are protected from HIV infection, while cells infected with a control lentivirus targeting luciferase (LUC) are not. HIV infection was measured by intracellular staining of p24 by flow cytometry.

Silencing HIV Replication in Primary Cells by Infection with Lentiviruses Encoding Small Hairpin RNAs Although small modified RNAs are preferable for use as a microbicide, other siRNA delivery strategy have been investigated. These strategies utilize infection by self-inactivating lentiviruses that express small hairpin RNAs (shRNA) processed by Dicer inside cells into siRNAs. These lentiviruses offer the potential to create a stable antiviral state after integration of the lentivirus into cellular chromosomes (Qin, X F, et al. (2003). *Proc Natl Acad Sci, USA,* 100, 183-188; Stewart, S A, et al. (2003). *RNA,* 9, 493-501). In the self-inactivating lentiviral vector, sequences were inserted that target HIV sequences in the LTR, rev, gag and vif genes, as well as those sequences that target the HIV co-receptor, CCR5, to produce HIV-specific shRNAs. Primary monocyte-derived macrophages infected with all of these shRNA lentiviruses are resistant to HV infection (FIG. 4). In addition, when $CD34^+$ hematopoietic stem cells are infected with these lentiviruses and then allowed to differentiate into macrophages in vitro, they are resistant to HIV infection.

Optimization of in vitro Delivery Strategies to Silence CCR5 with Duplex siRNAs in Murine Macrophages, Dendritic Cells, T Cells and Female Genital Mucosa.

In order for siRNAs to be utilized therapeutically in vivo, siRNAs need to survive in nuclease-rich biological fluids and tissues, have a favorable half-life, and be delivered into cells in a functional state. The half-life of unmodified duplex siRNAs after intravenous injection is measured only in seconds, since most of the material is rapidly cleared by the kidney. Although this short serum half-life may be less of a problem for topical use as a microbicide, a short half-life in the vagina will interfere with effective delivery. Moreover, unmodified, naked duplex siRNAs are not taken up efficiently in vitro by macrophages or monocyte-derived DCs (FIG. 3) without a transfection reagent or other specialized delivery method despite their phagocytic properties. Although epithelial LCs are less mature and more phagocytic than cultured DCs, it is unlikely that they will be efficiently transduced without a delivery method.

Identification of Mouse siRNAs that Silence CCR5 in vitro.

siRNAs that target CCR5 expression in murine hematopoietic cells are developed. CCR5 was chosen as a host target because it is the co-receptor involved in sexual transmission of HIV and CCR5 is considered a nonessential gene, since individuals with the Δ32 mutation lacking functional CCR5 are immunologically competent (Kawamura, T, et al. (2003). *Proc Natl Acad Sci, USA,* submitted). Candidate duplex siRNAs targeting murine CCR5 are identified and synthesized using the Tuschl algorithm (Elbashir, S M, et al. (2002). *Methods,* 26, 199-213). Preferably, a sequence with AA (or less preferably NA) followed by 19 nucleotides and then TT (although the last feature is optional) is chosen. The candidate sequence should also have a GC content of 35-70% and be at least 75 nucleotides downstream from the ATG initiation site. A final feature is that the sequence lack homology with any other genes based on, e.g. a blast search. Using the Tuschl algorithm, the majority of sequences effectively silence; with 4 trial sequences, a 100% success rate targeting ten distinct cellular or viral targets has been achieved (Novina, C D, et al. (2002). *Nat Med,* 8, 681-686; Song, E, et al. (2003). *J Virol,* 77, 7174-7181; Song, E, et al. (2003). *Nat Med,* 9, 347-351; Fan, Z, et al. (2003). *Cell,* 112, 659-672; Fan, Z, et al. (2003). *Nat Immunol,* 4, 145-153). Four candidate murine CCR5 sequences for targeting based on NCBI reference sequence NM_009917 (GI No:31542355, incorporated herein by reference; SEQ ID NO:11) have been identified:

```
(1) starting codon 450, sense:
5'-GUGUAGUCACUUGGGUGGUdTdT-3',     (SEQ ID NO:12)

antisense:
5'-ACCACCCAAGUGACUACACdTdT-3';     (SEQ ID NO:13)

(2) starting codon 823, sense:
5'-UAGACUAGACCAGGCCAUGdTdT-3';,    (SEQ ID NO:14)

antisense:
5'-CAUGGCCUGGUCUAGUCUAdTdT-3';     (SEQ ID NO:15)

(3) starting codon 958, sense:
5'-ACGCUUUUGCAAACGGUGUdTdT-3';,    (SEQ ID NO:16)

antisense:
5'-ACACCGUUUGCAAAAGCGUdTdT-3';     (SEQ ID NO:17)

(4) starting codon 992, sense:
5'-GACAAUCCUGAUCGUGUAAdTdT-3';,    (SEQ ID NO:18)

antisense:
5'-UUACACGAUCAGGAUUGUCdTdT-3'.     (SEQ ID NO:19)
```

Duplex siRNAs are commercially synthesized (Dharmacon), deprotected and annealed following the manufacturer's protocol and tested in vitro by transfecting the mouse macrophage cell line RAW 264.7 using oligofectamine as described (Novina, CD, et al. (2002). *Nat Med,* 8, 681-686; Song, E, et al. (2003). *J Virol,* 77, 7174-7181; Song, E, et al. (2003). *Nat Med,* 9, 347-351). Control cells are mock transfected or transfected with irrelevant control siRNAs (scrambled or GFP). Transfection efficiency is verified in wells transfected in parallel with FITC-labeled control siRNA. Two days after transfection, silencing is evaluated by flow cytometry analysis using the PE-conjugated mouse CCR5 antibody C34-3448 (PharMigen). The kinetics of silencing are analyzed for each of the siRNAs that silence CCR5 expression by at least 60%. siRNAs that silence in RAW 264.7 cells are next tested for silencing of CCR5 in transfected mouse macrophages (derived from adherent BALB/c splenocytes) and bone-marrow derived dendritic cells (prepared from the femurs of BALB/c mice as described (Feng, H, et al. (2001). *Blood,* 97, 3505-3512; Feng, H, et al. (2002). *Blood,* 100, 4108-4115; Feng, H, et al. (2003). *Blood,* 101, 245-252119-121)). Flow cytometry analysis will compare expression of the silenced gene CCR5 with co-staining for unsilenced lineage specific markers (CD14 and CD11c, respectively) as well as other cell surface markers expressed on these cells, such as CD80 and CD86. Cleavage of the target mRNAs and specificity of silencing will be verified for effective CCR5 siRNAs by RNase protection assay (RPA) using RNA prepared from siRNA-transfected and control treated macrophages and DCs using the mCR-5 multiprobe template set (PharMingen), which simultaneously analyzes mRNA for 6 chemoline receptors and 2 housekeeping genes (Alkhatib G, et al. (1996) *Science,* 272, 1955-1958).

If delivery of siRNAs is successful in macrophages and/or DCs, a similar analysis is performed using as targets nylon wool-separated splenic T cells, which are either resting or have been activated with conA. Experimentation has shown that transduction of T cells with the tat peptide yields a 50% frequency of transduction of activated human PBMC-derived T cells with Cy5-labeled siRNA.

Delivery and Silencing of CCR5 in Murine Macrophages, DCs and T Cells in vitro using Modified siRNAs.

Two anti-CCR5 siRNAs with the strongest and most prolonged silencing in transfected murine DCs as unmodified siRNAs, identified above, are chosen for further modifications to enhance stability and delivery. Each of these strategies is analyzed in vitro using RAW 264.7 cells followed by analysis with adherent monocytes, activated macrophages and bone marrow-derived DCs, as described above for unmodified siRNAs. The transduction and silencing in these cells at various stages of activation and differentiation are assessed since different strategies may have different effects depending on the state of the cell. Kinetics and dose response experiments allow quantitative comparisons between different delivery and silencing strategies as to strength and durability of silencing. The efficiency of transduction is analyzed using flow cytometry to detect and quantify the mean fluorescence intensity (MFI) of incorporated Cy5-labeled siRNAs for those constructs in which the 5' end of the sense strand is available. If it is not feasible to fluorescently label the siRNA (because the 5' end has been modified), the efficiency of transduction is determined by measuring silencing of CCR5 via flow cytometry, confirmed by immunoblot. Flow cytometry is preferable to immunoblot since it provides information on a per cell basis and can distinguish between inefficient delivery (i.e. by distinguishing distinct populations of silenced and non-silenced cells) and inefficient silencing in all cells.

A number of siRNA modification strategies are evaluated in order to achieve (1) enhancment of nuclease resistance and in vivo half-life and (2) targeting delivery to macrophages, DCs and T cells. Nuclease-resistant siRNAs can be prepared by modifying the 2'-OH of the sugar of some nucleotide residues by replacement with a 2'-O-Me group, protecting the 3' and 5' ends with inverted 3'-3' deoxyabasic sugars and adding phosphorothioate linkages between some of the residues (Usman, N, and Blatt, L M. (2000). *J Clin Invest,* 106, 1197-1202). These modifications do not interfere with in vitro silencing and prolong the in vivo half-life to days after intravenous or subcutaneous delivery without any known toxicity. Moreover the 5' or 3' end of the sense strand of the oligonucleotide can also be linked to other chemical moieties (such as polyethylene glycol) to enhance intravenous half-life further or to provide cell-specific targeted delivery. Modification of the sense strand will not interfere with gene silencing.

Bypassing transfection to achieve efficient delivery of siRNAs to macrophages and T cells has been achieved by mixing the siRNAs with a basic tat peptide (for example, residues 49-57: RKKRRQRRR; SEQ ID NO:16). The optimal ratio of tat peptide to siRNA has been determined and is compared to another basic peptide from *Drosophila,* the *Antennapedia* gene (residues 43-58; SEQ ID NO:20) (Prochiantz, A. (1996). *Curr Opin Neurobiol,* 6, 629-634; Moy, P, et al. 1996). *Molecular Biotechnology,* 6, 105-113; Kim, D T, et al (1997). *J Immunol,* 159, 1666-1668; Suzuki, T, et al. (2002). *J Biol Chem,* 277, 2437-2443). Delivery and silencing is compared between mixtures of peptide and siRNAs and covalently linked peptide-sense strands. An activated thiol at the 5' end of the sense stand is covalently linked to a cysteine residue added to the C terminal of the cationic peptides. Internalization via these peptides bypasses the endocytic pathway and therefore lessens the danger of degradation in the harsh lysosomal environment. Moreover, coupling antisense oligonucleotides to the Antennapedia peptide reduces the concentration required for biological efficacy by 1000-fold (Allinquant, B et al. (1995). *J Cell Biol,* 128, 919-927). A recent study demonstrates the feasibility of this approach using a peptide (MPG) derived from the fusion domain of HIV gp41 to deliver siRNAs into a variety of cell lines (Simeoni, F, et al. (2003). *Nucleic Acids Res,* 31, 2717-2724). This peptide is particularly attractive for the purpose of an HIV microbicide since it serves not only to deliver siRNAs, but at the same time act as an HIV fusion inhibitor to block viral entry. Therefore, the activity of MPG-siRNA in blocking HIV infection with the other peptide-siRNA pairs is compared.

Several strategies for specifically targeting DCs and macrophages are investigated, taking advantage of the unique properties of these cells, which are constantly sampling the environment and have special receptors for uptake of anionic polymers and phosphatidyl serine (PS) on apoptotic cells. The efficiency of uptake of soluble siRNA is compared with that of siRNA packaged into liposomes using different ratios of lipid to siRNA. Liposome composition is also modified to incorporate varying concentrations of PS to enhance uptake via the PS receptor used for the recognition and phagocytosis of apoptotic cells (Fadok, V A, et al. (2000). *Nature,* 405, 85-90; Fadok, V A, and Chimini, G. (2001). *Semin Immunol,* 13, 365-372; Hoffmann, P R, et al. (2001). *J Cell Biol,* 155, 649-659; Huynh, M L, et al. (2002). *J Clin Invest,* 109, 41-50). To produce liposomes, phospholipids in chloroform/methanol (90:10) are dried under nitrogen, resuspended in PBS containing various concentrations of duplex Cy5-labeled siRNA and sonicated for 3 hours at 4° C. The liposomes are added to plated MDMs (~105 cells/well) using approximately 1 uM/well with rocking for 1 hour (Huynh, M L, et al. (2002). *J Clin Invest,* 109, 41-50). The transfection efficiency is determined after overnight culture and washing by epifluorescence microscopy and quantitated by flow cytometry. The transfection conditions are optimized as to the ratio of PS/phosphatidyl choline (PC), the ratio of lipid/siRNA and the amount of lipid added/105 cells. The use of PS liposomes is particularly suitable since macrophage engulfinent via the PS receptor promotes an anti-inflammatory response by increasing TGF-β1 secretion (Huynh, M L, et al. (2002). *J Clin Invest,* 109, 41-50). Therefore if the macrophages are successfully transfected, not only will the proinflammatory cytokines be silenced, but the macrophage will also be induced to secrete anti-inflammatory cytokines. Another modification comprising adding a polyG tail 5-10 nucleotides in length to the 5' end of the sense strand of the siRNA, to enhance uptake via the macrophage scavenger receptor is assessed (Srividya, S, et al. (2000). *Biochem Biophys Res Commun,* 268, 772-777).

In vivo Delivery of Modified siRNAs in Mice

The modified siRNAs with the best delivery to DCs in vitro, identified above, are advanced for further testing in female mice. The modified siRNAs (together with unmodified siRNAs and control siRNAs not targeting CCR5) are introduced into the vaginas of anesthetized female mice kept prone for 5-10 minutes to increase absorption. The siRNAs are administered at a concentration ~50 ug/200 ul mixed in PBS and/or various human vaginal products such as KY jelly or nonoxynol-9 containing spermicide or emulsified with liposomes as described above. Oligofectamine is also assessed for efficient in vivo delivery. In addition, plugging the vagina with Vaseline is analyzed to determine if local delivery is enhanced. Myeloid cell-GFP-transgenic mice are utilized for these experiments with Cy5-labeled siRNA (Faust, N, et al. (2000). *Blood,* 96, 719-726). In these mice, GFP is expressed from a lysozomal promoter in all myeloid cells which allows determination of delivery by epifluorescence microscopy to macrophages and myeloid DCs, the cells of special interest for HIV transmission.

To determine which cells are transduced after vaginal treatment, mice are sacrificed 1 and 2 days later and are analyzed for Cy5-labeled siRNA and CCR5 expression in tissue sections obtained from dissected preparations of the uterus, cervix and vagina and draining lymph nodes (to detect emigrated LCs) by fluorescence microscopy and in cell suspensions by flow cytometry. For histological analysis, following perfusion, dissected organs are embedded in OCT medium and snap frozen in liquid N2. Signs of in vivo toxicity, such as disruption of epithelial integrity, inflammatory infiltration or cellular necrosis/apoptosis are noted. Sections are fixed and stained for CCR5 as well as with cell specific markers to identify keratinocytes (keratin), macrophages (CD14) and DCs (CD11c and MIDC-8), and/or markers that are expressed on both macrophages and DCs and are upregulated after maturation, such as CD40, CD80 and CD86, in order to determine which cells are efficiently or inefficiently transduced. The fixation method is chosen that best preserves the signal of small RNAs, readily determined by those skilled in the art. Alexa-conjugated secondary antibodies are used to optimize fluorescence intensity. Tissue sections are analyzed using a multiphoton Bio-Rad Radiance 2000 laser scanning microscope (Olympus BX50WI) enhanced with a Ti Sapphire Tsunami laser (Spectra-Physics). Quantification is performed using a Lasersharp 3.2 image acquisition and analysis software program. Tissue sections are also analyzed for specific mRNA by in situ hybridization using FITC-labeled CCR5 oligonucleotide probes and analyzed by epifluorescence microscopy as described (Song, E, et al. (2003). *J Virol,* 77, 7174-7181). Individual cells are identified by counterstaining with Texas Red-X phalloidin or cell type-specific antibodies as above. The fluorescence analysis of protein expression and post-transcriptional mechanisms of gene silencing is performed by Northern blotting of RNA isolated from tissues and selected purified cell types, probed for CCR5 mRNA and siRNAs.

To complement the tissue staining studies, single cell suspensions are analyzed by flow cytometry and immunohistochemistry to identify differences in silencing in different cell types. Using endotoxin-free collagenase and DNase, single cell suspensions are prepared from each of the tissues harvested separately and analyzed for CCR5 expression by flow cytometry. If accurate quantitation of mRNA is needed, a real-time PCR protocol is developed and used to analyze CCR5 MRNA in immunomagnetically selected cell populations. Modified Northern blots are used to analyze expression of siRNAs in particular cell populations. In order to avoid losing siRNAs during isolation, Trizol purified siRNAs are pelleted, washed in 70% EtOH, air-dried and analyzed on 15% TBE-urea gels probed with end-labeled oligonucleotide encoding the sense strand of the siRNA (Song, E, et al. (2003). *J Virol,* 77, 7174-7181).

Differences in delivery or silencing (quantitated by mean fluorescence intensity in flow cytometry or by densitometry/phosphorimager analysis of immunoblots or Northern blots) between cell types or tissues or between different cells during development will be analyzed for statistical significance by the Student's t-test.

siRNA Delivery Strategies to Silence CCR5 in the Human Skin Blister Model of Human Vaginal Epithelium A model system to assess delivery of siRNA in vitro for use as a microbicide is the human vaginal epithelium skin blister model (Kawamura T, et al. (2000). *J Exp Med,* 192, 1491-1500). In this model, suction blisters are generated from cleaned skin, which split the lamina lucida and contain only the epithelium, consisting of keratinocytes and LCs, responsible for direct transmission. These immature LCs have the properties of vaginal or cervical DCs and can mature and crawl out of the tissues, like LCs in vivo. The epithelia is treated with microbicidal agents and/or virus in an oriented manner and analyzed in situ. This model is advantageous since it requires little manipulation in order to "mature" the LCs and it has been validated to mimic the parameters of transmission.

The human suction blister explant model, NCI98, is used to assess siRNA delivery and gene silencing of LCs in situ in intact epithelium. These experiments are performed using siRNAs that are naked RNA duplexes, chemically modified duplexes and/or duplexes mixed with delivery vehicles. To reduce sample variability, donors are chosen who lack the Δ32 CCR5 mutation (a-2359A/G single nucleotide polymorphism (SNP)) and are homozygous for the wild-type CCR5 promoter to minimize differences in CCR5 expression or coreceptor activity (Kawamura, T, et al. (2003). *Proc Natl Acad Sci, USA*, submitted). Blistering through the lamina lucida of the epithelium is induced by heat and vacuum suction applied to shaved and cleansed skin of the anterior thigh of healthy human volunteers as described (Kawamura T, et al. (2000). *J Exp Med*, 192, 1491-1500). These epithelial sheets contain keratinocytes and LCs, but are devoid of macrophages and T cells. The roofs of the ~1 cm diameter blisters (20 blisters/donor) are sterilely removed with scissors, washed gently with PBS and placed with the stratum corneum surface side down (to mimic drug application in vivo) in contact with 50 µl droplets containing naked, modified or delivery formulated siRNAs. The effect of delivery to the oppositely oriented blister (basal epithelial surface down) is also compared.

All candidate human siRNA preparations for delivery are evaluated for delivery, silencing and protection from $HIV_{BaL}$ infection of MDM and monocyte-derived dendritic cells (MDDC) in vitro. MDMs are the adherent cells that develop after normal donor PBMCs have been plated for 2 hr at 37° C. at $2\times10^6$/well in 24 well plates. MDMs are washed and incubated overnight with 1 µM modified siRNA. In addition activated macrophages and MDDC are prepared by incubation for 7 day in medium containing 20% human AB serum and 5 ng/ml GM-CSF, with or without 500 U/ml IL-4 and/or TNF-α (Friedman, R S, et al. (2000). *J Virol*, 74, 9987-9993). Addition of IL-4 promotes differentiation into cells with DC4ike properties, while TNF-α provides a further maturation signal. Although these cells are more mature than the epithelial LCs in uninflamed epithelia, activated cells are present in inflamed genital tissue. These experiments will test the delivery methods of this invention to macrophages and DCs at different states of differentiation, which may differ in their susceptibility to some of the delivery methods. For example, siRNA delivery via basic peptide was efficient in GM-CSF-activated macrophages (FIG. 3) but not in GM-CSF plus IL-4 treated MDDCs. For each construct unmodified CCR5 duplex siRNA known to silence in vitro is compared to a scrambled siRNA and/or control siRNA. The siRNAs are synthesized based on the human CCR5 target sequence that was shown to silence CCR5 and inhibit HIV infection of macrophages (sense 5'-P.CUCUGCUUCGGUGUCGUCGAAAdTdT-3' (SEQ ID NO:1); antisense 5'-P.UUUCGACACCGAAGCA-GAGdTdT-3' (SEQ ID NO:2)) (Song, E, et al. (2003). *J Virol*, 77, 7174-7181). CCR5 siRNAs modified at the ends or by substitutions on the sugars to enhance stability or for intracellular delivery, as described above, may be utilized. siRNAs may be fluorescently labeled at the 5'-end of the sense strand with Cy3 or fluorescein using the Ambion Silencer siRNA labeling kit to enable easy detection of intracellular siRNAs by flow cytometry of individual cell suspensions (prepared by trypsinization after siRNA treatment) or fluorescence microscopy. Verification that modifications to the 5'-end of the sense strand does not interfere with siRNA silencing function is determined in vitro for each construct by comparing the MFI of CCR5 expression in human MDMs treated with paired unlabeled or labeled siRNAs targeting CCR5. Delivery of fluorescently labeled naked siRNA in the presence or absence of oligofectamine is used as a positive and negative control for delivery. A similar analysis is performed using modified siRNAs targeting p24, using the sequences previously demonstrated to be effective (Novina, C D, et al. (2002). *Nat Med*, 8, 681-686; Song, E, et al. (2003). *J Virol*, 77, 7174-7181).

siRNA preparations that pass the in vitro screen, described above, will be analyzed in duplicate blisters obtained from at least 2 donors. The maximal incubation time with siRNA-containing droplets, e.g., the longest time that doesn't cause cell death of keratinocytes or LCs, disrupt the integrity of the epithelial sheets (determined by impermeability to small molecule dyes), or change the phenotypic properties of LCs, is chosen. Preliminary analysis indicates this time is approximately 2 hours, since LCs in these explants begin to express the maturation marker CD83 after that time.

Treated skin blisters are analyzed for delivery of siRNAs and silencing of CCR5 in situ by epifluorescence microscopy of fixed sections for fluorescently labeled siRNAs and by immunohistochemistry for CCR5 and cell-type specific antibodies for MHC class I and II, CD80, CD86, CD4, CD83, CD14 or isotype control. A parallel analysis examines the same parameters by flow cytometry staining for fluorescently labeled siRNAs and for CCR5 with cell-type specific antibodies and isotype control antibodies in "crawl out" LCs which are obtained 1-3 day after culture (Kawamura T, et al. (2000). *J Exp Med*, 192, 1491-1500). A real-time PCR protocol to quantify CCR5 mRNA in crawl out LCs is developed based on methods known to those skilled in the art.

The skin blister model described above is useful for the assessment of delivery of siRNA. It may take a day before reduced mRNA levels are translated into reduced amounts of CCR5 protein, which is important for the evaluation of CCR5 siRNA silencing in HIV challenge experiments. This is less of a problem for evaluating viral targets such as gag, where there is no intracellular mRNA or protein to begin with. A protocol is developed to challenge these explants by treating explants for 20-60 minutes at 37° C. with the optimal stabilized p24 siRNA (with and without CCR5 siRNA) by draping the explants over droplets containing siRNAs. The explants are gently removed and draped over droplets containing siRNAs containing $HIV_{BaL}$ at various dilutions and cultured for an additional hour at 37° C. The explants are washed extensively to remove cell-free virus and floated in cultures containing 20% human AB serum. HV infection in LCs is assessed by p24 ELISA of culture supernatants (harvested every other day), by intracellular staining for p24 and transmission electron microscopy for visualization of virions (Kawamura T, et al. (2000) *J Exp Med*, 192, 1491-1500). Some explant cultures are co-cultured with human CD4+ T cells obtained form normal donor PBMCs by immunomagnetic negative selection to amplify the infection and measure the transmission of HIV to T cells by in situ treated LCs. The viability and differentiation status of the LCs (and keratinocytes) in the explants are carefully monitored. All treated cultures are controlled by parallel analysis of mock-treated cultures, uninfected cultures, scrambled or control siRNAs, as well as unmodified siRNAs delivered by oligofectamine. In addition, positive controls include samples treated with 100 nM aminooxypentane-RANTES, an effective inhibitor of infection (Kawamura T, et al. (2000). *J Exp Med*, 192, 1491-1500.).

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for inhibiting HIV entry into CCR5-expressing cells comprising administering intravaginally to an individual a formulation comprising one or more siRNAs directed against CCR5 and a pharmaceutically acceptable carrier, wherein the one or more siRNAs comprise SEQ ID NO: 1 and SEQ ID NO: 2.

2. The method of claim 1, wherein the pharmaceutically acceptable carrier comprises a component selected from the group consisting of a basic peptide, nonoxynol-9-containing spermicide, vaginal lubricant, liposomes, and combinations thereof.

* * * * *